United States Patent
Haruta

(10) Patent No.: US 11,311,615 B2
(45) Date of Patent: Apr. 26, 2022

(54) VACCINE COMPOSITIONS

(71) Applicant: SHIN NIPPON BIOMEDICAL LABORATORIES, LTD., Kagoshima (JP)

(72) Inventor: Shunji Haruta, Kagoshima (JP)

(73) Assignee: SHIN NIPPON BIOMEDICAL LABORATORIES, LTD., Kagoshima (JP)

( * ) Notice: Subject to any disclaimer, the term of this patent is extended or adjusted under 35 U.S.C. 154(b) by 58 days.

(21) Appl. No.: 15/760,341

(22) PCT Filed: Sep. 16, 2016

(86) PCT No.: PCT/JP2016/004225
§ 371 (c)(1),
(2) Date: Mar. 15, 2018

(87) PCT Pub. No.: WO2017/047089
PCT Pub. Date: Mar. 23, 2017

(65) Prior Publication Data
US 2018/0326039 A1 Nov. 15, 2018

Related U.S. Application Data

(60) Provisional application No. 62/219,215, filed on Sep. 16, 2015.

(51) Int. Cl.
| | |
|---|---|
| A61K 9/19 | (2006.01) |
| A61K 39/145 | (2006.01) |
| A61K 47/38 | (2006.01) |
| A61K 47/36 | (2006.01) |
| A61K 9/16 | (2006.01) |
| A61K 9/00 | (2006.01) |
| A61K 9/14 | (2006.01) |
| A61K 39/12 | (2006.01) |
| A61K 39/00 | (2006.01) |

(52) U.S. Cl.
CPC .......... *A61K 39/145* (2013.01); *A61K 9/0043* (2013.01); *A61K 9/145* (2013.01); *A61K 9/146* (2013.01); *A61K 9/1682* (2013.01); *A61K 9/19* (2013.01); *A61K 39/12* (2013.01); *A61K 47/36* (2013.01); *A61K 47/38* (2013.01); *A61K 2039/5252* (2013.01); *A61K 2039/543* (2013.01); *A61K 2039/55511* (2013.01); *A61K 2039/55583* (2013.01); *A61K 2039/70* (2013.01); *C12N 2760/16134* (2013.01)

(58) Field of Classification Search
None
See application file for complete search history.

(56) References Cited

U.S. PATENT DOCUMENTS

| | | | |
|---|---|---|---|
| 5,871,739 A | 2/1999 | Inoue | |
| 2002/0120228 A1* | 8/2002 | Maa | A61K 9/0021 604/57 |
| 2009/0238797 A1 | 9/2009 | Lang et al. | |
| 2010/0291115 A1* | 11/2010 | Silvestrini | A61K 9/006 424/184.1 |
| 2013/0129781 A1* | 5/2013 | Nagata | A61K 9/0043 424/206.1 |
| 2013/0273120 A1 | 10/2013 | Nagata et al. | |
| 2014/0294872 A1 | 10/2014 | Barr et al. | |

FOREIGN PATENT DOCUMENTS

| | | |
|---|---|---|
| EP | 0770398 A2 | 5/1997 |
| EP | 1854478 A1 | 11/2007 |
| EP | 2035033 A1 | 3/2009 |
| EP | 2689785 A1 | 1/2014 |
| EP | 2773778 A1 | 9/2014 |
| JP | 2009539821 A | 11/2009 |
| JP | 2013523602 A | 6/2013 |
| JP | 2014533240 A | 12/2014 |
| WO | WO-2007131972 A1 | 11/2007 |
| WO | WO-2007144724 A1 | 12/2007 |
| WO | WO-2011129120 A1 | 10/2011 |
| WO | WO-2013066769 A1 | 5/2013 |
| WO | WO-2017047089 A1 | 3/2017 |

OTHER PUBLICATIONS

International search report and written opinion dated Dec. 6, 2016 for PCT Application No. JP-2016/004225.

\* cited by examiner

*Primary Examiner* — Craig D Ricci
(74) *Attorney, Agent, or Firm* — Wilson Sonsini Goodrich & Rosati

(57) ABSTRACT

Provided herein are vaccine compositions for example in a dry powder form for intranasal delivery, and their preparation methods. Also provided are methods of using vaccine compositions, for example in stimulating mucosal or systemic immune responses by delivering the vaccine compositions intranasally.

33 Claims, 5 Drawing Sheets

[Fig. 1]
Cake Appearances of Freeze-Dried Antigens
Undesirable Cake Appearance
Cracking
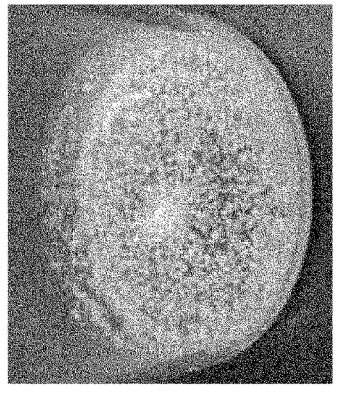
Melt-back
Shrinkage
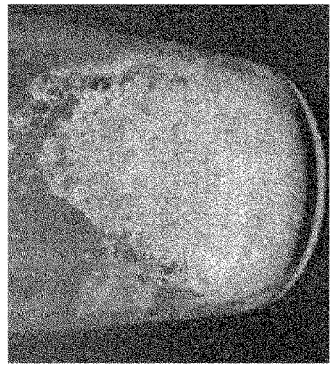
Collapse
Desirable Cake Appearance
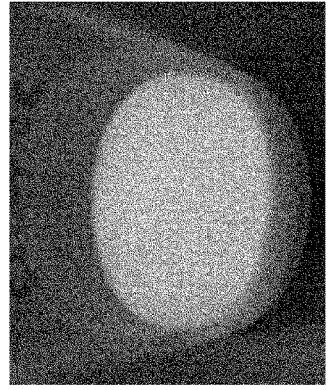

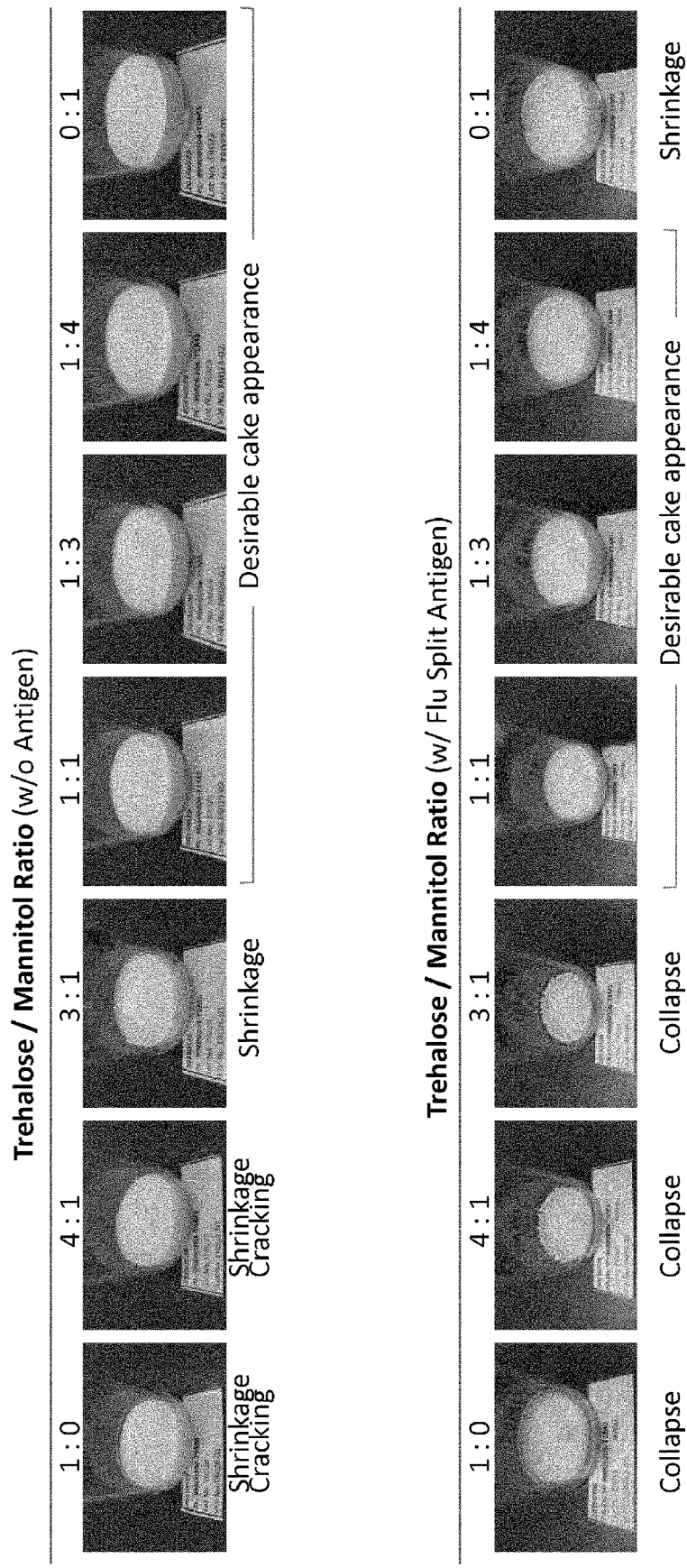

[Fig. 3]
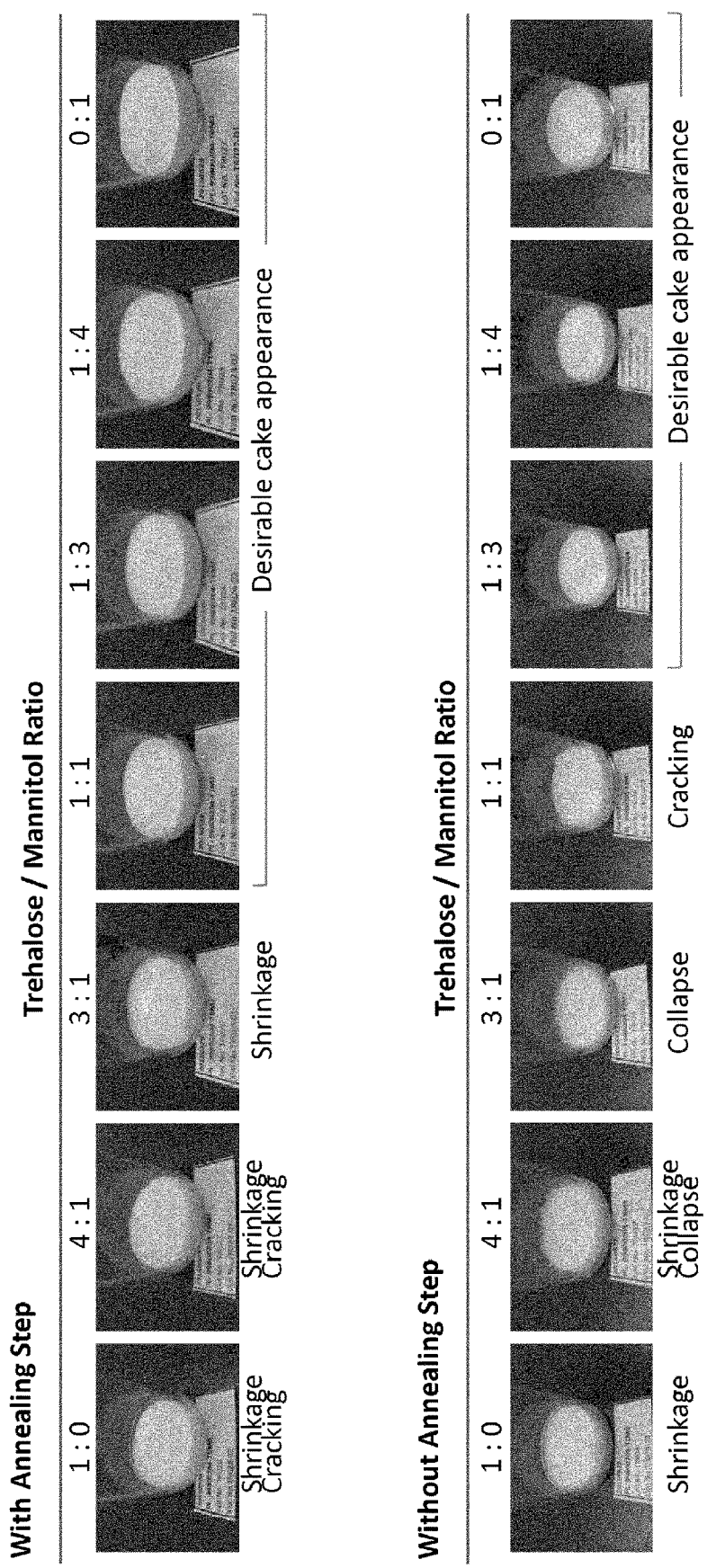

[Fig. 4]
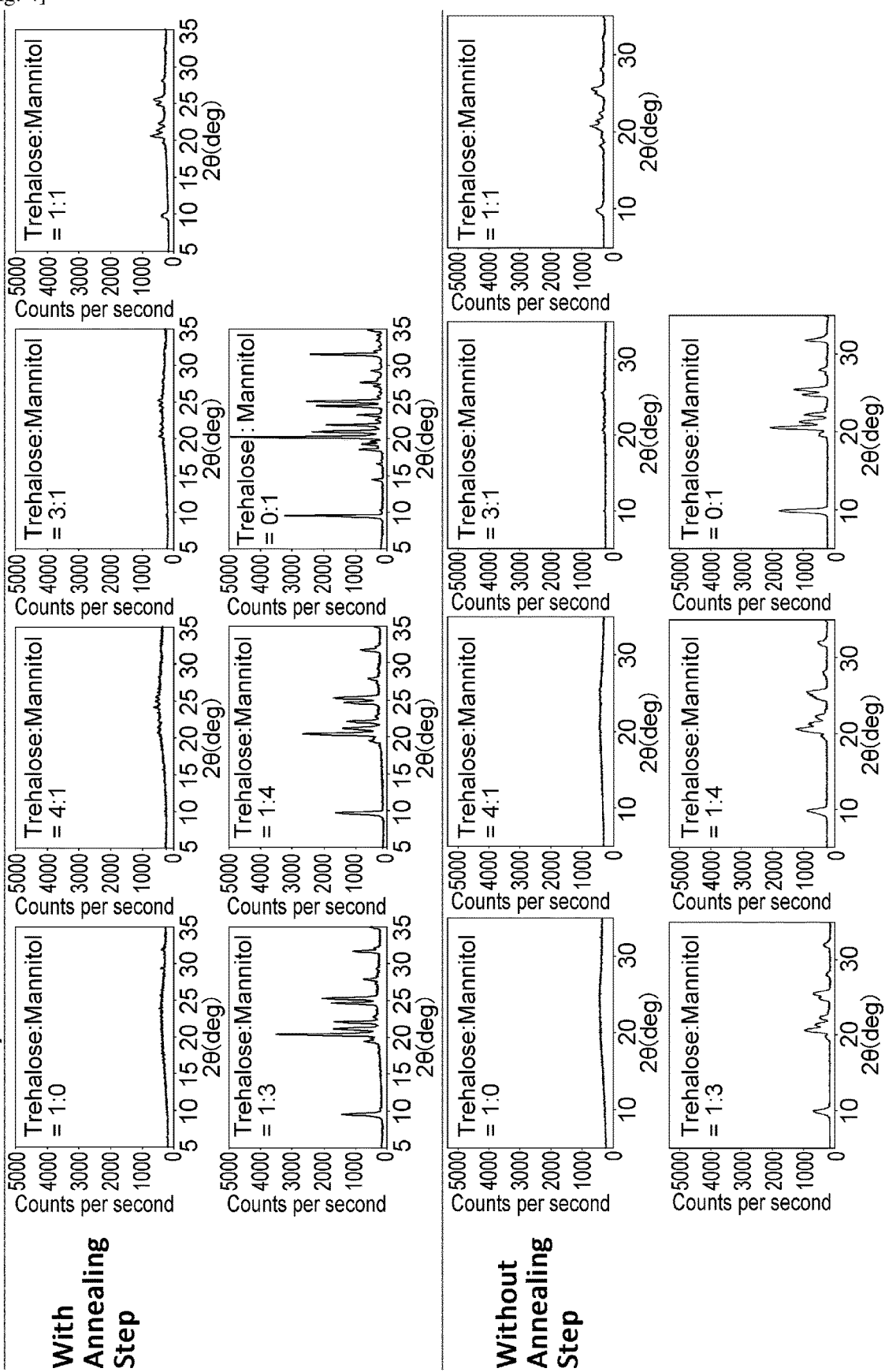

[Fig. 5]
Crystallinity of Mannitol in Freeze-Dried Powders with Annealing
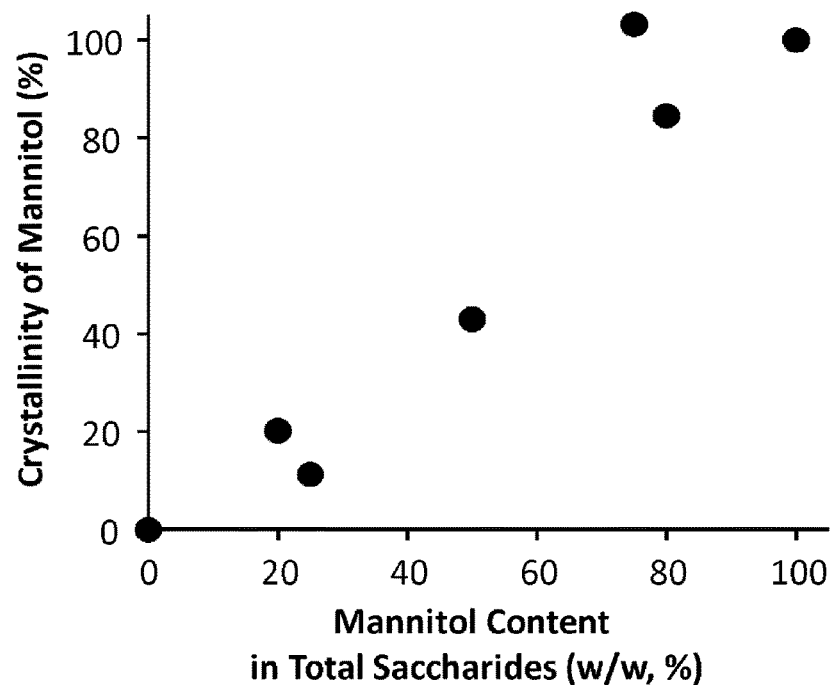

VACCINE COMPOSITIONS

SUMMARY OF INVENTION

In some aspects, the present disclosure provides for a composition, comprising an antigen; a first saccharide; a second saccharide; and a third saccharide that comprises microcrystalline cellulose, wherein a weight ratio of the first saccharide to the second saccharide is from about 3:2 to about 1:10, or a molar ratio of the first saccharide to the second saccharide is from about 3:1 to about 1:5. In some embodiments, the composition is a powder composition. In some embodiments, the composition comprises one, two, three, four, or more antigens. In some embodiments, the composition is a monovalent vaccine or multivalent vaccine. In some embodiments, the composition is a bivalent, trivalent, or quadrivalent vaccine. In some embodiments, the vaccine is an influenza vaccine. In some embodiments, the dry powder composition has a water content less than 6% w/w. In some embodiments, the water content is measured by the Karl Fischer's method. In some embodiments, the first saccharide, the second saccharide, and the third saccharide are all different. In some embodiments, when administered intranasally to a human, the composition produces a serum immune response. In some embodiments, when administered intranasally to a human, the composition stimulates the production of serum Immunoglobulin G (IgG) antibodies. In some embodiments, when administered intranasally to a human, the composition produces a mucosal immune response. In some embodiments, when administered intranasally to a human, the composition stimulates the production of mucosal secretory Immunoglobulin A (sIgA) antibodies. In some embodiments, when administered intranasally to a human, the composition produces a cellular immune response. In some embodiments, the composition is suitable for mucosal delivery. In some embodiments, the composition is suitable for intranasal delivery. In some embodiments, the composition is in a form of cake. In some embodiments, the composition has the weight ratio of the first saccharide to the second saccharide that is about: 1:1, 1:2, 1:3, 1:4, or 1:7. In some embodiments, the composition has the molar ratio of the first saccharide to the second saccharide which is about: 2:1, 1:1, 2:3, 1:2, or 2:7. In some embodiments, the first saccharide comprises an oligosaccharide or a polysaccharide. In some embodiments, the first saccharide comprises a disaccharide. In some embodiments, the second saccharide comprises a monosaccharide. In some embodiments, at least 80% (w/w) of the first saccharide is in an amorphous form. In some embodiments, at least 20% (w/w) of the second saccharide is in a crystal form. In some embodiments, the first saccharide comprises trehalose, inulin, sucrose, maltose, isomaltose, maltotriose, pullulan, raffinose, or any combination thereof. In some embodiments, the second saccharide comprises mannitol, sorbitol, glucose, galactose, or any combination thereof. In some embodiments, the microcrystalline cellulose has an average particle size of from about 10 microns to about 100 microns as measured by sifting, sieving or laser diffraction. In some embodiments, the antigen comprises a viral antigen, a bacterial antigen, or a combination thereof. In some embodiments, the antigen comprises live attenuated virus, whole inactivated virus, split virus, subunit antigen, virosome, antigenic protein, antigenic peptide, virus-like particle with antigenic protein, virus-like particle with antigenic peptide, cold-adapted live virus, killed whole bacteria, attenuated bacteria, bacterial toxoid, bacterial antigenic polysaccharide, nucleotide, phage, or any combination thereof. In some embodiments, the antigen comprises influenza virus, respiratory syncytial virus, Rhinovirus, Coronavirus, Adenovirus, metapneumovirus, bocavirus, parainfluenza virus, measles virus, rubella virus, varicella zoster virus, herpes simplex virus, human herpes virus, Parvovirus B19, Enterovirus, mumps virus, or any combination thereof. In some embodiments, the antigen comprises human papillomavirus, poliovirus, Rotavirus, Norwalk virus, sapovirus, Astrovirus, or any combination thereof. In some embodiments, the antigen comprises West Nile virus, dengue virus, Ebola virus, Marburg virus, Crimean-Congo hemorrhagic fever virus, Lassa virus, hepatitis A virus, hepatitis B virus, hepatitis C virus, hepatitis D virus, hepatitis E virus, rabies virus, or any combination thereof. In some embodiments, the antigen comprises *Bordetella pertussis* toxoid, diphtheria toxoid, *Haemophilus influenzae* type b, *Mycobacterium tuberculosis*, *Streptococcus pneumoniae*, *Salmonella typhi*, *Yersinia pestis*, *Vibrio cholerae*, or any combination thereof. In some embodiments, the antigen comprises an influenza split virus. In some embodiments, the antigen comprises an influenza virosome. In some embodiments, the antigen comprises a whole inactivated influenza virus. In some embodiments, the composition further comprises an adjuvant. In some embodiments, the composition does not comprise an adjuvant.

In some aspects, the present disclosure provides for a method for generating any composition disclosed herein, comprising freeze-drying a liquid with annealing.

In some aspects, the present disclosure provides for a method for generating a composition, comprising: freeze-drying a liquid with annealing to form a solid, wherein the liquid comprises an antigen, a first saccharide, and a second saccharide; and blending the solid with a third saccharide that comprises microcrystalline cellulose. In some embodiments, the first saccharide, the second saccharide, and the third saccharide are all different. In some embodiments, the drying comprises a first drying and a second drying. In some embodiments, a total amount of the first saccharide and the second saccharide is more than 40 mg per 1 mL of the liquid. In some embodiments, a total amount of the first saccharide and the second saccharide is about: 50 mg, 75 mg, or 100 mg per 1 mL of the liquid. In some embodiments, the liquid further comprises a salt. In some embodiments, the liquid has a salt concentration ranging from about 0.25% to about 3% (w/w) of the liquid. In some embodiments, the liquid has a salt concentration ranging from about: 0.25, 0.5, or 1% (w/w) of the liquid. In some embodiments, the liquid has a pH ranging from about 7 to about 8. In some embodiments, the liquid has a pH of about 7.4. In some embodiments, the liquid comprises a buffering agent. In some embodiments, the liquid comprises a buffering agent that comprises at least one selected from the group consisting of phosphate buffered saline, potassium phosphate, sodium phosphate, disodium hydrogenphosphate, and potassium dihydrogenphosphate. In some embodiments, the liquid comprises a phosphate buffered saline. In some embodiments, the annealing is conducted at a temperature of from about −20° C. to about −28° C. In some embodiments, the annealing is conducted at about −23° C. In some embodiments, the annealing is conducted for about 1 hour to about 5 hours. In some embodiments, the annealing is conducted for about 3 hours. In some embodiments, the first drying is conducted at a temperature of from about −15° C. to about −40° C. In some embodiments, the first drying is conducted at about −35° C. In some embodiments, the first drying is conducted for about 30 hours to about 90 hours. In some embodiments, the first drying is conducted for about 54 hours. In some embodiments, the second drying is conducted at a temperature of from about 25° C. to about 60° C. In some embodiments, the second drying is conducted at about 30° C. In some embodiments, the second drying is conducted for about 1 hour to about 10 hours. In some embodiments, the second drying is conducted for about 4 hours. In some embodiments, the drying is conducted under a vacuum of about 105 mTorr or lower. In some embodiments, the method further comprises pre-freezing the liquid at about −30° C.

In some aspects, the present disclosure provides for a composition made by any method disclosed herein.

In some aspects, the present disclosure provides for a method, comprising administering to a subject any composition disclosed herein. In some aspects, the present disclosure provides for a method, comprising administering to a subject a composition generated by any method disclosed herein. In some embodiments, the method prevents an infection. In some embodiments, the method stimulates a mucosal secretory Immunoglobulin A (sIgA) immune response. In some embodiments, the method stimulates a serum Immunoglobulin G (IgG) immune response. In some embodiments, the method stimulates a cellular immune response. In some embodiments, the subject is a human. In some embodiments, the subject is a subject in need thereof. In some embodiments, the administering is mucosal. In some embodiments, the administering is intranasal.

In some aspects, the present disclosure provides for a device comprising any composition disclosed herein. In some aspects, the present disclosure provides for a device comprising any composition generated by any method disclosed herein. In some embodiments, the device is for mucosal use. In some embodiments, the device is for intranasal use. In some embodiments, the device is configured for a single use.

In some aspects, the present disclosure provides for a method of using any device disclosed herein to a subject, comprising releasing a composition in the device to a nostril, e.g., one or two nostrils, of the subject. In some embodiments, the subject is a human.

INCORPORATION BY REFERENCE

All publications, patents, and patent applications mentioned in this specification are herein incorporated by reference to the same extent as if each individual publication, patent, or patent application was specifically and individually indicated to be incorporated by reference in their entirety.

BRIEF DESCRIPTION OF DRAWINGS

FIG. 1 illustrates desirable and undesirable cake appearances of freeze-dried antigens.

FIG. 2 illustrates effects of trehalose/mannitol ratios on cake appearance of freeze-dried antigens.

FIG. 3 illustrates effects of annealing on cake appearance of freeze-dried antigens.

FIG. 4 illustrates X-ray powder diffraction patterns of freeze-dried powders with and without annealing.

FIG. 5 illustrates crystallinity of mannitol in freeze-dried powders with annealing.

DESCRIPTION OF EMBODIMENTS

Detailed Description

Unless defined otherwise, all technical and scientific terms used herein have the same meaning as commonly understood by one of the ordinary skill in the art to which this invention belongs. Although any methods and materials similar or equivalent to those described herein can be used in the practice or testing of the formulations or unit doses herein, some methods and materials are now described. Unless mentioned otherwise, the techniques employed or contemplated herein are standard methodologies. The materials, methods and examples are illustrative only and not limiting.

The details of one or more inventive embodiments are set forth in the accompanying drawings, the claims, and the description herein. Other features, objects, and advantages of the inventive embodiments disclosed and contemplated herein can be combined with any other embodiment unless explicitly excluded.

Unless otherwise indicated, open terms for example "contain," "containing," "include," "including," and the like mean comprising.

The singular forms "a", "an", and "the" are used herein to include a single or plural references, e.g., one or more, unless the context clearly dictates otherwise. Accordingly, unless the contrary is indicated, the numerical parameters set forth in this application are approximations that may vary depending upon the desired properties sought to be obtained by the present invention.

Unless otherwise indicated, some embodiments herein contemplate numerical ranges. When a numerical range is provided, unless otherwise indicated, the range includes the range endpoints. Unless otherwise indicated, numerical ranges include all values and subranges therein as if explicitly written out.

The term "about" means plus or minus 15% of a referenced numeric value, unless indicated otherwise.

The term "desirable appearance" of a cake means an appearance of neither shrinkage, cracking, collapse, nor melt-back, for example a uniform or intact structure.

The term "annealing" means a process of holding a substance at a temperature above a freezing temperature for a defined period of time to allow formation of crystals, for example holding a sample at an elevated temperature for a period of time while still keeping the sample frozen (so that large ice crystals can grow).

I. Overview

In some aspects, the present disclosure provides for a composition, comprising an antigen; a first saccharide; a second saccharide; and a third saccharide that comprises microcrystalline cellulose, wherein a weight ratio of the first saccharide to the second saccharide is from about 3:2 to about 1:20, for example, from about 3:2 to about 1:10, from about 3:2 to about 1:11, from about 3:2 to about 1:12, from about 3:2 to about 1:13, from about 3:2 to about 1:14, from about 3:2 to about 1:15, from about 3:2 to about 1:16, from about 3:2 to about 1:17, from about 3:2 to about 1:18, or from about 3:2 to about 1:19, or a molar ratio of the first saccharide to the second saccharide is from about 3:1 to about 1:10, for example, from about 3:1 to about 1:5, from about 3:1 to about 1:6, from about 3:1 to about 1:7, from about 3:1 to about 1:8, or from about 3:1 to about 1:9. In some embodiments, the composition is a powder composition. In some embodiments, the composition comprises one, two, three, four, five, six, seven, eight, nine, ten, or more antigens. In some embodiments, the composition is a monovalent vaccine. In some embodiments, the composition is a multivalent vaccine. In some embodiments, the composition is a bivalent vaccine. In some embodiments, the composition is a trivalent vaccine. In some embodiments, the composition is a quadrivalent vaccine. In some embodiments, the composition is a pentavalent vaccine. In some embodiments, the vaccine is an influenza vaccine. In some embodiments, the dry powder composition has a water content less than 6% w/w, for example, less than 5.3%, less than 5%, less than 4%, less than 3%, less than 2%, less than 1%, less than 0.5%, less than 0.1%, about 0.1-5%, about 0.1-4%, about 0.1-3%, about 0.1-2%, or about 0.1-1%. In some embodiments, the water content is measured by the Karl Fischer's method. In some embodiments, the first saccharide, the second saccharide, and the third saccharide are all different. In some embodiments, when administered intranasally to a human, the composition produces a serum immune response. In some embodiments, when administered intranasally to a human, the composition stimulates the production of serum Immunoglobulin G (IgG) antibodies. In some embodiments, when administered intranasally to a human, the composition produces a mucosal immune response. In some embodiments, when administered intranasally to a human, the composition stimulates the production of mucosal secretory Immunoglobulin A (sIgA) antibodies. In some embodiments, when administered intranasally to a human, the composition produces a cellular immune response. In some embodiments, the composition is suitable for mucosal delivery. In some embodiments, the composition is suitable for intranasal delivery. In some embodiments, the composition is in a form of cake. In some embodiments, the composition has the weight ratio of the first saccharide to the second saccharide that is about: 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, or 1:20. In some embodiments, the composition has the molar ratio of the first saccharide to the second saccharide which is about: 2:1, 1:1, 2:3, 1:2, 2:5, 1:3, 2:7, 1:2, 2:9, 1:5, 2:11, 1:6, 2:13, 1:7, 2:15, 1:8, 2:17, 1:9, 2:19, or 1:10. In some embodiments, the first saccharide comprises an oligosaccharide or a polysaccharide. In some embodiments, the first saccharide comprises a disaccharide. In some embodiments, the second saccharide comprises a monosaccharide. In some embodiments, at least 80%, 85%, 90%, 95%, or 98% (w/w) of the first saccharide is in an amorphous form. In some embodiments, at least 20%, 30%, 40%, 50%, 60%, 70%, 80%, 90%, or 95% (w/w) of the second saccharide is in a crystal form. In some embodiments, the first saccharide comprises trehalose, inulin, sucrose, maltose, isomaltose, maltotriose, pullulan, raffinose, or any combination thereof. In some embodiments, the second saccharide comprises mannitol, sorbitol, glucose, galactose, or any combination thereof. In some embodiments, the microcrystalline cellulose has an average particle size of from about 10 microns to about 100 microns, for example about 10 to 20 microns, about 10 to 30 microns, about 10 to 40 microns, about 10 to 50 microns, about 10 to 60 microns, about 10 to 70 microns, about 10 to 80 microns, about 10 to 90 microns, or about: 15, 20, 25, 30, 35, 40, 45, 50, 55, 60, 65, 70, 75, 80, 85, 90, or 95 microns, as measured by sifting, sieving or laser diffraction. In some embodiments, the antigen comprises a viral antigen, a bacterial antigen, or a combination thereof. In some embodiments, the antigen comprises live attenuated virus, whole inactivated virus, split virus, subunit antigen, virosome, antigenic protein, antigenic peptide, virus-like particle with antigenic protein, virus-like particle with antigenic peptide, cold-adapted live virus, killed whole bacteria, attenuated bacteria, bacterial toxoid, bacterial antigenic polysaccharide, nucleotide, phage, or any combination thereof. In some embodiments, the antigen comprises influenza virus, respiratory syncytial virus, Rhinovirus, Coronavirus, Adenovirus, metapneumovirus, bocavirus, parainfluenza virus, measles virus, rubella virus, varicella zoster virus, herpes simplex virus, human herpes virus, Parvovirus B19, Enterovirus, mumps virus, or any combination thereof. In some embodiments, the antigen comprises human papillomavirus, poliovirus, Rotavirus, Norwalk virus, sapovirus, Astrovirus, or any combination thereof. In some embodiments, the antigen comprises West Nile virus, dengue virus, Ebola virus, Marburg virus, Crimean-Congo hemorrhagic fever virus, Lassa virus, hepatitis A virus, hepatitis B virus, hepatitis C virus, hepatitis D virus, hepatitis E virus, rabies virus, or any combination thereof. In some embodiments, the antigen comprises *Bordetella pertussis* toxoid, diphtheria toxoid, *Haemophilus influenzae* type b, *Mycobacterium tuberculosis, Streptococcus pneumoniae, Salmonella typhi, Yersinia pestis, Vibrio cholerae*, or any combination thereof. In some embodiments, the antigen comprises an influenza split virus. In some embodiments, the antigen comprises an influenza virosome. In some embodiments, the antigen comprises a whole inactivated influenza virus. In some embodiments, the composition further comprises an adjuvant. In some embodiments, the composition does not comprise an adjuvant.

In some aspects, the present disclosure provides for a method for generating any composition disclosed herein, comprising freeze-drying a liquid with annealing.

In some aspects, the present disclosure provides for a method for generating a composition, comprising: freeze-drying a liquid with annealing to form a solid, wherein the liquid comprises an antigen, a first saccharide, and a second saccharide; and blending the solid with a third saccharide that comprises microcrystalline cellulose. In some embodiments, the first saccharide, the second saccharide, and the third saccharide are all different. In some embodiments, the drying comprises a first drying and a second drying. In some embodiments, a total amount of the first saccharide and the second saccharide is more than 40 mg per 1 mL of the liquid, for example, more than: 50, 55, 60, 65, 70, 75, 80, 85, 90, 95, 100, 110, 120, 130, 140, 150, 160, 170, 180, 190, or 200 mg, or about: 45-200 mg, 45-150 mg, or 45-100 mg, or about: 50, 55, 60, 65, 70, 75, 80, 85, 90, 95, 100, 110, 120, 130, 140, 150, 160, 170, 180, 190, or 200 mg. In some embodiments, a total amount of the first saccharide and the second saccharide is about: 50 mg, 75 mg, or 100 mg per 1 mL of the liquid. In some embodiments, the liquid further comprises a salt. In some embodiments, the liquid has a salt concentration ranging from about 0.25% to about 3%, about 0.1-10%, about 0.1-5%, about 0.1-4%, about 0.1-3%, about 0.1-2%, or about 0.1-1% (w/w) of the liquid. In some embodiments, the liquid has a salt concentration ranging from about: 1%, 0.1%, 0.25%, 0.5%, 1.5%, 2%, 3%, 4%, 5%, 6%, 7%, 8%, 9%, or 10% (w/w) of the liquid. In some embodiments, the liquid has a pH ranging from about 7 to about 8, about 6-8, about 6-9, about 5-8, about 5-9, or about 5-10. In some embodiments, the liquid has a pH of about: 7.4, 5, 5.5, 6, 6.2, 6.4, 6.6, 6.8, 7, 7.2, 7.6, 7.8, 8, 8.5, 9, 9.5, or 10. In some embodiments, the liquid comprises a buffering agent. In some embodiments, the liquid comprises a buffering agent that comprises at least one selected from the group consisting of phosphate buffered saline, potassium phosphate, sodium phosphate, disodium hydrogenphosphate, and potassium dihydrogenphosphate. In some embodiments, the liquid comprises a phosphate buffered saline. In some embodiments, the annealing is conducted at a temperature of from about −20° C. to about −28° C., about −20° C. to about −40° C., −20° C. to about −50° C., −20° C. to about −60° C., −20° C. to about −70° C., about −10° C. to about −20° C., about −10° C. to about −30° C., about −10° C. to about −40° C., −10° C. to about −50° C., −10° C. to about −60° C., or −10° C. to about −70° C. In some embodiments, the annealing is conducted at about: −23° C., −5° C., −10° C., −15° C., −20° C., −25° C., −30° C., −35° C., −40° C., −45° C., −50° C., −60° C., or −70° C. In some embodiments, the annealing is conducted for about 1 hour to about 5 hours, or about 1-10 hours. In some embodiments, the annealing is conducted for about: 0.5, 1, 2, 3, 4, 5, 6, 7, 8, 9, or 10 hours. In some embodiments, the first drying is conducted at a temperature of from about −15° C. to about −40° C., about −15° C. to about −50° C., about −15° C. to about −60° C., about −15° C. to about −70° C., −25° C. to about −40° C., about −25° C. to about −50° C., about −25° C. to about −60° C., or about −25° C. to about −70° C. In some embodiments, the first drying is conducted at about: −35° C., −5° C., −10° C., −15° C., −20° C., −25° C., −30° C., −40° C., −45° C., −50° C., −60° C., or −70° C. In some embodiments, the first drying is conducted for about 30 hours to about 90 hours, about 10-150 hours, about 10-100 hours, about 20-90 hours, about 30-80 hours, about 40-70 hours, or about 50-60 hours. In some embodiments, the first drying is conducted for about: 54, 3, 5, 10, 15, 20, 25, 30, 35, 40, 45, 50, 55, 60, 65, 70, 75, 80, 85, 90, 95, 100, 110, 120, 130, 140, or 150 hours. In some embodiments, the second drying is conducted at a temperature of from about 25° C. to about 60° C., about 20° C. to about 30° C., about 20° C. to about 35° C., 20° C. to about 40° C., 20° C. to about 45° C., or 20° C. to about 50° C. In some embodiments, the second drying is conducted at about: 30° C., 5° C., 10° C., 15° C., 20° C., 25° C., 30° C., 40° C., 45° C., 50° C., 55° C., or 60° C. In some embodiments, the second drying is conducted for about 1 hour to about 10 hours, about 3-5 hours, about 2-6 hours, or about 1-7 hours. In some embodiments, the second drying is conducted for about: 0.5, 1, 2, 3, 4, 5, 6, 7, 8, 9, or 10 hours. In some embodiments, the drying is conducted under a vacuum of about 105 mTorr or lower. In some embodiments, the method further comprises pre-freezing the liquid at about: −30° C., −5° C., −10° C., −15° C., −20° C., −25° C., −35° C., −40° C., −45° C., −50° C., −60° C., or −70° C.

In some aspects, the present disclosure provides for a composition made by any method disclosed herein.

In some aspects, the present disclosure provides for a method, comprising administering to a subject any composition disclosed herein. In some aspects, the present disclosure provides for a method, comprising administering to a subject a composition generated by any method disclosed herein. In some embodiments, the method prevents an infection. In some embodiments, the method stimulates a mucosal secretory Immunoglobulin A (sIgA) immune response. In some embodiments, the method stimulates a serum Immunoglobulin G (IgG) immune response. In some embodiments, the method stimulates a cellular immune response. In some embodiments, the subject is a human. In some embodiments, the subject is a subject in need thereof. In some embodiments, the administering is mucosal. In some embodiments, the administering is intranasal.

In some aspects, the present disclosure provides for a device comprising any composition disclosed herein. In some aspects, the present disclosure provides for a device comprising any composition generated by any method disclosed herein. In some embodiments, the device is for mucosal use. In some embodiments, the device is for intranasal use. In some embodiments, the device is configured for a single use. In some embodiments, the device is configured for multiple uses.

In some aspects, the present disclosure provides for a method of using any device disclosed herein to a subject, comprising releasing a composition in the device to a nostril, e.g., one or two nostrils, of the subject. In some embodiments, the subject is a human.

In some aspects, a composition disclosed herein is in a solid form (e.g., a powder form) and retains antigenic potency as in a corresponding liquid form. In some aspects, a composition or freeze-dried antigen disclosed herein can have cake characteristics, including a desirable appearance, e.g., neither shrinkage, cracking, collapse nor melt-back (e.g., having an uniform structure); sufficiently dry; easily friable cake to result in fine powder; and adequate moisture resistance. In some aspects, a composition disclosed herein can be uniformly and widely delivered from a device.

In some aspects, vaccine compositions disclosed herein enable to increase moisture resistance, keep antigenic potency in a powder form compared to a liquid form and be delivered uniformly on the mucosa. In some embodiments, provided herein are vaccine compositions (e.g., in dry powder) for effective mucosal delivery, preparation methods, and methods for preventing an infection by way of mucosal and systemic immune responses stimulated by mucosal delivery of vaccine which lead to fulfill the above requirements.

In some aspects, provided herein are methods for preparing compositions or freeze-dried antigens. In some embodiments, the preparation method can comprise a step of generating a liquid antigen mixture containing one or more antigens (e.g., a whole inactivated influenza virus) with one or more agents (e.g., saccharides and buffer). A liquid antigen mixture can be freeze-dried (e.g., comprising annealing step) to generate a freeze-dried antigen. The freeze-dried antigen(s) can have cake characteristics desired for vaccine compositions (e.g., in dry powder) for mucosal delivery, e.g., neither shrinkage, cracking, collapse nor melt-back; sufficiently dry; easily friable cake to result in fine powder; and adequate moisture resistance. The excipient used for mucosal delivery can be microcrystalline cellulose which is a water-insoluble and non-gel forming excipient. The excipient can improve flowability of the powder, increase moisture resistance of the freeze-dried antigen, be uniformly and widely deliver the powder on the mucosa, be effectively deliver the powder from a delivery device, and prolong retention time of the powder on the mucosa.

In some aspects, a vaccine composition (e.g., in dry powder) described herein can be stable at room temperature. This is an advance over liquid influenza vaccines, which are unstable at room temperature and can require expensive storage and distribution under refrigerated conditions (e.g., cold-chain distribution). A liquid antigen mixture containing the first saccharide selected from trehalose, inulin, sucrose, maltose, isomaltose, maltotriose pullulan or raffinose, and the second saccharide selected from mannitol, sorbitol, glucose or galactose, is prepared. A method described herein can provide a freeze-dried antigen with cake characteristics desired for vaccine compositions (e.g., in dry powder) for mucosal delivery, e.g., neither shrinkage, cracking, collapse nor melt-back, and sufficiently dry, easily friable cake to result in fine powder, and adequate moisture resistance, using the first saccharide selected from trehalose, inulin, sucrose, maltose, isomaltose, maltotriose pullulan or raffinose, and the second saccharide selected from mannitol, sorbitol, glucose or galactose.

In some aspects, a powderized antigen can be produced by freeze-drying method comprising freezing step(s), annealing step(s) and drying steps which are completed inside a freeze drying equipment without a quick freezing step. The freeze-dried antigen can be blended with one or more excipients, such as a water-insoluble and non-gel-forming nasal carrier (e.g., microcrystalline cellulose) and/or a fluidizer (e.g., tribasic calcium phosphate). The excipient can improve flowability of the freeze-dried antigen, increase moisture resistance of the freeze-dried antigen, be uniformly and widely deliver the vaccine composition (e.g., in dry powder) from a delivery device.

In some aspects, a method provided herein can allow for improving the efficacy of a vaccine. The methods can comprise steps for generating a dry vaccine powder compositions that can stimulate a local immune response, for example, a mucosal immune response (e.g., involving mucosal sIgA). sIgA can provide cross-protection against mutated influenza viruses (e.g., a vaccine composition (e.g., in dry powder) can be used as a pandemic influenza vaccine) and/or viruses which have undergone genetic drift. A vaccine composition (e.g., in dry powder), e.g., a dry nasal influenza powder formulation, can induce protection in distal mucosal sites. For example, introduction of a vaccine of the present disclosure at the nasal mucosa can lead to protection (e.g., sIgA production in the upper respiratory tract, the lower respiratory tract, the gastrointestinal tract, and vagina). A vaccine composition (e.g., in dry powder) can stimulate a systemic immune response (e.g., producing serum IgG). In some embodiments, a vaccine composition (e.g., in dry powder) does not comprise an adjuvant.

In some aspects, the present disclosure provides a vaccine composition (e.g., in dry powder) for mucosal delivery comprising: one or more viral or bacterial antigens; the first saccharide added to powderize liquid antigens, which is selected from trehalose, inulin, sucrose, maltose, isomaltose, maltotriose pullulan or raffinose; the second saccharide added to powderize liquid antigens, which is selected from mannitol, sorbitol, glucose or galactose, and microcrystalline cellulose with a specific surface area of at least 1.3 m$^2$/g and a mean particle size of less than 100 microns as an excipient which is added to blend with the powderized antigens. In some embodiments, at least one of said one or more antigens is live attenuated virus, whole inactivated virus, split virus, subunit antigen, virosome, antigenic protein, antigenic peptide, virus-like particle with antigenic protein, virus-like particle with antigenic peptide, cold-adapted live virus, killed whole bacteria, attenuated bacteria, bacterial toxoid, bacterial antigenic polysaccharide, nucleotide or phage. In some embodiments, at least one of said one or more antigens is influenza virus, respiratory syncytial virus, Rhinovirus, Coronavirus, Adenovirus, metapneumovirus, bocavirus, parainfluenza virus, measles virus, rubella virus, varicella zoster virus, herpes simplex virus, human herpes virus, Parvovirus B19, Enterovirus, or mumps virus. In some embodiments, at least one of said one or more antigens is human papillomavirus, poliovirus, Rotavirus, Norwalk virus, sapovirus, or Astrovirus. In some embodiments, at least one of said one or more antigens is West Nile virus, dengue virus, Ebola virus, Marburg virus, Crimean-Congo hemorrhagic fever virus, Lassa virus, hepatitis A virus, hepatitis B virus, hepatitis C virus, hepatitis D virus, hepatitis E virus, or rabies virus. In some embodiments, at least one of said one or more antigens is *Bordetella pertussis* toxoid, diphtheria toxoid, *Haemophilus influenzae* type b, *Mycobacterium tuberculosis, Streptococcus pneumoniae, Salmonella typhi, Yersinia pestis, Vibrio cholerae*. In some embodiments, at least one of said one or more antigens is whole inactivated influenza virus antigen. In some embodiments, a total amount of said the first saccharide and said the second saccharide is more than 50 mg per 1 mL of liquid antigen mixture. In some embodiments, said second saccharide is added at a ratio of 1 to between 0.8 to 3% (w/w) to the first saccharide added in the liquid antigen mixture. In some embodiments, said liquid antigen is in phosphate buffer saline with a salt concentration of 0.25 to 3% (w/v). In some embodiments, the vaccine composition (e.g., in dry powder) further comprises adjuvant. In some embodiments, the vaccine composition (e.g., in dry powder) is for intranasal delivery.

In some aspects, the present disclosure provides a method for generating a vaccine composition (e.g., in dry powder) for mucosal delivery comprising: preparing a liquid preparation comprising one or more antigens, the first saccharide elected from trehalose, inulin, sucrose, maltose, isomaltose, maltotriose pullulan or raffinose, and the second saccharide selected from mannitol, sorbitol, glucose or galactose, and freeze-drying the said liquid antigen mixture without a quick freezing step and with annealing step(s); and blending the freeze-dried antigen with at least microcrystalline cellulose with a specific surface area of at least 1.3 m$^2$/g and a mean particle size of less than 100 microns as an excipient to generate the vaccine composition (e.g., in dry powder). In some embodiments, at least one of said one or more antigens is live attenuated virus, whole inactivated virus, split virus, subunit antigen, virosome, antigenic protein, antigenic peptide, virus-like particle with antigenic protein, virus-like particle with antigenic peptide, cold-adapted live virus, killed whole bacteria, attenuated bacteria, bacterial toxoid, bacterial antigenic polysaccharide, nucleotide or phage. In some embodiments, at least one of said one or more antigens is influenza virus, respiratory syncytial virus, Rhinovirus, Coronavirus, Adenovirus, metapneumovirus, bocavirus, parainfluenza virus, measles virus, rubella virus, varicella zoster virus, herpes simplex virus, human herpes virus, Parvovirus B19, Enterovirus, or mumps virus. In some embodiments, at least one of said one or more antigens is human papillomavirus, poliovirus, Rotavirus, Norwalk virus, sapovirus, or Astrovirus. In some embodiments, at least one of said one or more antigens is West Nile virus, dengue virus, Ebola virus, Marburg virus, Crimean-Congo hemorrhagic fever virus, Lassa virus, hepatitis A virus, hepatitis B virus, hepatitis C virus, hepatitis D virus, or hepatitis E virus, or rabies virus. In some embodiments, at least one of said one or more antigens is *Bordetella pertussis* toxoid, diphtheria toxoid, *Haemophilus influenzae* type b, *Mycobacterium tuberculosis, Streptococcus pneumoniae, Salmonella typhi, Yersinia pestis, Vibrio cholerae*. In some embodiments, at least one of said one or more antigens is whole inactivated influenza virus antigen. In some embodiments, said first saccharide is added at an amount of 5 to 250 mg per 1 mL of liquid antigen mixture. In some embodiments, said second saccharide is added at a ratio of 1 to, 0.8 to 3 (w/w) to the first saccharide added in the liquid antigen mixture. In some embodiments, the most of said first saccharide is formed as amorphous after freeze-drying antigens. In some embodiments, at least 20% (w/w) of said second saccharide is formed as crystal after freeze-drying antigens. In some embodiments, the vaccine composition (e.g., in dry powder) does not comprise adjuvant. In some embodiments, the vaccine composition (e.g., in dry powder) is for intranasal delivery.

In some aspects, the present disclosure provides method of defensing infections in a subject to an antigen by administering a vaccine composition (e.g., in dry powder) for mucosal delivery to the subject, wherein said the vaccine composition (e.g., in dry powder) for mucosal delivery comprises one or more antigens and wherein a powderized antigen in said the vaccine composition (e.g., in dry powder)

is generated by freeze-drying method without a quick freezing step and with annealing step(s). In some embodiments, a defense is based on stimulations of a mucosal sIgA immune response as well as serum IgG immune response in a subject to an antigen. In some embodiments, a defense is based on stimulations of a mucosal sIgA immune response and cellular immune response as well as serum IgG immune response in a subject to an antigen. In some embodiments, said vaccine composition (e.g., in dry powder) comprises live attenuated virus, whole inactivated virus, split virus, subunit antigen, virosome, antigenic protein, antigenic peptide, virus-like particle with antigenic protein, virus-like particle with antigenic peptide, cold-adapted live virus, killed whole bacteria, attenuated bacteria, bacterial toxoid, bacterial antigenic polysaccharide, nucleotide or phage. In some embodiments, said vaccine composition (e.g., in dry powder) comprises influenza virus, respiratory syncytial virus, Rhinovirus, Coronavirus, Adenovirus, metapneumovirus, bocavirus, parainfluenza virus, measles virus, rubella virus, varicella zoster virus, herpes simplex virus, human herpes virus, Parvovirus B19, Enterovirus, or mumps virus. In some embodiments, said vaccine composition (e.g., in dry powder) comprises human papillomavirus, poliovirus, Rotavirus, Norwalk virus, sapovirus, or Astrovirus. In some embodiments, said vaccine composition (e.g., in dry powder) comprises West Nile virus, dengue virus, Ebola virus, Marburg virus, Crimean-Congo hemorrhagic fever virus, Lassa virus, hepatitis A virus, hepatitis B virus, hepatitis C virus, hepatitis D virus, or hepatitis E virus, or rabies virus. In some embodiments, said vaccine composition (e.g., in dry powder) comprises *Bordetella pertussis* toxoid, diphtheria toxoid, *Haemophilus influenzae* type b, *Mycobacterium tuberculosis, Streptococcus pneumoniae, Salmonella typhi, Yersinia pestis, Vibrio cholerae*. In some embodiments, said vaccine composition (e.g., in dry powder) comprises whole inactivated influenza virus antigen. In some embodiments, said vaccine composition (e.g., in dry powder) comprises whole inactivated influenza viral antigen. In some embodiments, said powder vaccine composition does not comprise adjuvant. In some embodiments, said vaccine composition (e.g., in dry powder) is for intranasal delivery.

In some aspects, the present disclosure provides intranasal delivery device for a vaccine composition (e.g., in dry powder) generated by a method disclosed herein.

In some aspects, the present disclosure relates to vaccine compositions, e.g., in dry powder for intranasal administration, and their preparation methods. In some embodiments, the vaccine compositions effectively induce mucosal immunity as well as systemic immunity. In some embodiments, vaccine compositions herein are used for mucosal delivery. In some embodiments, vaccine compositions herein are highly resistant to moisture. In some embodiments, vaccine compositions herein have equivalent or higher antigenic potency in a powder form compared to a corresponding liquid vaccine composition. In some embodiments, vaccine compositions herein are delivered uniformly or non-uniformly on the mucosa.

Disclosed herein is a vaccine composition (e.g., in dry powder) comprising: one or more antigens, saccharide needed for powderization of antigens, one or more buffers for powderization of antigens, and one or more excipients for mucosal delivery. An antigen can be live attenuated virus, whole inactivated virus, split virus, subunit antigen, virosome, antigenic protein, antigenic peptide, virus-like particle with antigenic protein, virus-like particle with antigenic peptide, cold-adapted live virus, killed whole bacteria, attenuated bacteria, bacterial toxoid, bacterial antigenic polysaccharide, nucleotides and phage. The antigen can be influenza virus, respiratory syncytial virus, Rhinovirus, Coronavirus, Adenovirus, metapneumovirus, bocavirus, parainfluenza virus, measles virus, rubella virus, varicella zoster virus, herpes simplex virus, human herpes virus, Parvovirus B19, Enterovirus, or mumps virus, human papillomavirus, poliovirus, Rotavirus, Norwalk virus, sapovirus, or Astrovirus, West Nile virus, dengue virus, Ebola virus, Marburg virus, Crimean-Congo hemorrhagic fever virus, Lassa virus, hepatitis A virus, hepatitis B virus, hepatitis C virus, hepatitis D virus, or hepatitis E virus, or rabies virus, *Bordetella pertussis* toxoid, diphtheria toxoid, *Haemophilus influenzae* type b, *Mycobacterium tuberculosis, Streptococcus pneumoniae, Salmonella typhi, Yersinia pestis, Vibrio cholera*. The saccharide used for powderization of antigens can be the first saccharide selected from trehalose, inulin, sucrose, maltose, isomaltose, maltotriose pullulan or raffinose, and the second saccharide selected from mannitol, sorbitol, glucose or galactose. The buffer used for powderization of antigens can be a phosphate buffer saline. The excipient used for mucosal delivery can be microcrystalline cellulose which is a water-insoluble and non-gel forming excipient. A vaccine composition (e.g., in dry powder) described herein can be stable at room temperature and 60% relative humidity for at least 12 months.

Also provided herein is a method for generating a vaccine composition (e.g., in dry powder) comprising: preparing a liquid antigen mixture comprising antigen(s), saccharides and buffer(s); freeze-drying said liquid antigen mixture, wherein the freeze-drying comprise freezing step(s), annealing step(s) and drying step(s) without a quick freezing and spray freezing steps; blending the freeze-dried antigen(s) with one or more excipients to generate the vaccine composition (e.g., in dry powder). An antigen can be live attenuated virus, whole inactivated virus, split virus, subunit antigen, virosome, antigenic protein, antigenic peptide, virus-like particle with antigenic protein, virus-like particle with antigenic peptide, cold-adapted live virus, killed whole bacteria, attenuated bacteria, bacterial toxoid, bacterial antigenic polysaccharide, nucleotides and phage. The antigen can be influenza virus, respiratory syncytial virus, Rhinovirus, Coronavirus, Adenovirus, metapneumovirus, bocavirus, parainfluenza virus, measles virus, rubella virus, varicella zoster virus, herpes simplex virus, human herpes virus, Parvovirus B19, Enterovirus, or mumps virus, human papillomavirus, poliovirus, Rotavirus, Norwalk virus, sapovirus, or Astrovirus, West Nile virus, dengue virus, Ebola virus, Marburg virus, Crimean-Congo hemorrhagic fever virus, Lassa virus, hepatitis A virus, hepatitis B virus, hepatitis C virus, hepatitis D virus, or hepatitis E virus, or rabies virus, *Bordetella pertussis* toxoid, diphtheria toxoid, *Haemophilus influenzae* type b, *Mycobacterium tuberculosis, Streptococcus pneumoniae, Salmonella typhi, Yersinia pestis, Vibrio cholera*. The saccharide used for powderization of antigens can be the first saccharide selected from trehalose, inulin, sucrose, maltose, isomaltose, maltotriose pullulan or raffinose, and the second saccharide selected from mannitol, sorbitol, glucose or galactose. The buffer used for powderization of antigens can be a phosphate buffer saline. The excipient used for mucosal delivery can be microcrystalline cellulose which is a water-insoluble and non-gel forming excipient. The freeze-dried antigen(s) can have one or more of cake characteristics desired for vaccine composition (e.g., in dry powder) for mucosal delivery: neither shrinkage, cracking, collapse, nor melt-back; sufficiently dry; easily friable cake to result in fine powder; and adequate moisture resistance. The excipient used for mucosal delivery can be microcrystalline cellulose which can be a water-insoluble and non-gel forming excipient. The excipient can improve flowability of the powder, increase moisture resistance of the freeze-dried antigen, be uniformly and widely deliver the powder on the mucosa, be effectively deliver the powder from a delivery device, and prolong retention time of the powder on the mucosa. Some vaccine compositions (e.g., in dry powder) produced by the method herein do not comprise an adjuvant. The vaccine composition (e.g., in dry powder) can be stable at room temperature and 60% relative humidity for at least 12 months.

Another method provided herein is a method of stimulating mucosal immune response as well as systemic immune response against antigen(s) in a subject by administering a vaccine composition (e.g., in dry powder) comprising the antigen(s) to a subject, wherein the dry powder formulation is generated by freeze-drying with annealing step and without quick freezing and spray-freezing steps, and then blending excipients for mucosal delivery. An sIgA antibody produced based on the mucosal immune response can be stimulated at the site of administration and/or at a mucosal site other than the site of administration. Administration can be intranasal. An antigen can be live attenuated virus, whole inactivated virus, split virus, subunit antigen, virosome, antigenic protein, antigenic peptide, virus-like particle with antigenic protein, virus-like particle with antigenic peptide, cold-adapted live virus, killed whole bacteria, attenuated bacteria, bacterial toxoid, bacterial antigenic polysaccharide, nucleotides and phage. The antigen can be influenza virus, respiratory syncytial virus, Rhinovirus, Coronavirus, Adenovirus, metapneumovirus, bocavirus, parainfluenza virus, measles virus, rubella virus, varicella zoster virus, herpes simplex virus, human herpes virus, Parvovirus B19, Enterovirus, or mumps virus, human papillomavirus, poliovirus, Rotavirus, Norwalk virus, sapovirus, or Astrovirus, West Nile virus, dengue virus, Ebola virus, Marburg virus, Crimean-Congo hemorrhagic fever virus, Lassa virus, hepatitis A virus, hepatitis B virus, hepatitis C virus, hepatitis D virus, or hepatitis E virus, or rabies virus, *Bordetella pertussis* toxoid, diphtheria toxoid, *Haemophilus influenzae* type b, *Mycobacterium tuberculosis, Streptococcus pneumoniae, Salmonella typhi, Yersinia pestis, Vibrio cholera*. The saccharide used for powderization of antigens can be the first saccharide selected from trehalose, inulin, sucrose, maltose, isomaltose, maltotriose pullulan or raffinose, and the second saccharide selected from mannitol, sorbitol, glucose or galactose. The buffer used for powderization of antigens can be a phosphate buffer saline. The excipient used for mucosal delivery can be microcrystalline cellulose which is a water-insoluble and non-gel forming excipient. The excipient can improve flowability of the powder, increase moisture resistance of the freeze-dried antigen, be uniformly and widely deliver the powder on the mucosa, be effectively deliver the powder from a delivery device, and prolong retention time of the powder on the mucosa. Some vaccine compositions (e.g., in dry powder) produced by the method herein do not comprise an adjuvant. The vaccine composition (e.g., in dry powder) can be stable at room temperature and 60% relative humidity for at least 12 months.

Also provided herein is a device for administration of a vaccine composition (e.g., in dry powder) disclosed herein.

II. Liquid Antigen Mixture for Use in Generating Freeze-Dried Antigen

In some aspects, in order to generate a freeze-dried antigen in a vaccine composition (e.g., in dry powder), a liquid antigen mixture can be first generated. The liquid antigen mixture can comprise one or more antigens, one or more saccharides, and one or more buffers.

In some aspects, the volume of the liquid antigen mixture can be about 0.1 mL, 1.0 mL, 10 mL, 25 mL, 50 mL, 100 mL, 250 mL, 500 mL, 1 L, 10 L, 50 L, 100 L, 250 L, 500 L, or 1000 L. The volume of the liquid antigen mixture can be more than about 0.1 mL, 1.0 mL, 10 mL, 25 mL, 50 mL, 100 mL, 250 mL, 500 mL, 1 L, 10 L, 50 L, 100 L, 250 L, 500 L, or 1000 L. The volume of the liquid antigen mixture can be about 0.01-1 mL, about 1-10 mL, about 10-50 mL, about 50-100 mL, about 1-1000 mL, about 100-1000 mL, about 1-10 L, about 10-50 L, about 50-100 L, about 100-500 L, about 100-1000 L, or about 1-1000 L.

A. Antigen Components

In some aspects, a method of generating a vaccine composition (e.g., in dry powder) described herein can be used to produce a vaccine with a live attenuated virus, whole inactivated virus, split virus, subunit antigen, virosome, antigenic protein, antigenic peptide, virus-like particle with antigenic protein, virus-like particle with antigenic peptide, cold-adapted live virus, killed whole bacteria, attenuated bacteria, bacterial toxoid, bacterial antigenic polysaccharide, nucleotides and phage.

In some aspects, adaptation of a virus to growth in the cultured cells can be accompanied by a gradual loss of virulence for the natural host. Avirulence can be conferred, e.g., by accumulation of point mutations. Genetic engineering can be used to achieve viral attenuation by, e.g., generating temperature sensitive mutants, generating deletion mutants, site-directed mutagenesis, or generating live recombinant viruses.

In some aspects, a method of generating a vaccine composition (e.g., in dry powder) described herein can be used to produce a vaccine with a whole inactivated virus. Inactivated viruses can be generated, for example, by using ultraviolet light, low pH (e.g., acid, e.g., caprylic acid), pasteurization, solvents/detergents, sodium thiocyanate, formalin, beta-propiolactone, or ethylenimines. UV rays can damage DNA through by creating nucleic acid dimers, which can inactivate viruses by preventing the replication of genetic material. Some viruses denature upon exposure to low pH solutions. This method can be particularly effective when employed verses enveloped viruses. Pasteurization can inactivate viruses by means of temperature induced denaturation. Solvent/detergent inactivation is only effective against viruses enveloped in a lipid coat. The detergent used is typically Triton-X 100. Sodium thiocyanate can denature the protein coat of viruses, rendering the virus inactive. Formalin can chemically modify the surface proteins of the viral coat, which can prevent infection. Ethylenimines and beta-propiolactone can act on the nucleic acids of the virus while leaving the protein coat mostly unmodified. Inactivation can destroy infectivity of the virus while maintaining its immunogenicity. Multiple applications of inactivated virus can be administered to a subject.

In some aspects, a method of generating a vaccine composition (e.g., in dry powder) described herein can be used to produce a vaccine with one or more antigens (e.g., vaccine proteins) from one or more pathogens. An antigenic protein can be from any pathogen to which a vaccine is to be produced. For example, where the vaccine is to target influenza virus, an antigenic protein can be hemagglutinin (HA) and/or neuraminidase (NA). Hemagglutinin is an antigenic glycoprotein and a major surface protein of the influenza A virus. It mediates the biding between an influenza virus and the cell to be infected by binding to sialic acid-containing receptors on the surface of the cell. Viral particles bound to the surface of the cell are engulfed into endosomes. Inside the endosome, HA mediates a fusion of the viral membrane and the endosomal membrane, releasing the viral genome into the cell. Structurally, HA consists of three identical monomers organized into a helical coil. A function blocking antibody could inhibit either the cell binding or membrane fusing functions of HA. Neuraminidase is another glycoprotein found on the surface of an influenza virus. NAs are enzymes that function by cleaving sialic acid groups from glycoproteins. This cleavage seems to serve two functions: to prevent viral clumping and to release progeny viruses from the surface of a cell.

In some embodiments, a vaccine antigen can be HAL HA2, HA3, HA4, HA5, HA6, HA7, HA8, HA9, HA10, HA11, HA12, HA13, HA14, HA15, or HA16. In some embodiments, a vaccine antigen can be NA1, NA2, NA3, NA4, NA5, NA6, NA7, NA8, or NA9. A vaccine prepared from a HA and/or NA subtype can be used individually or in any combination. For example, two or more of the various HA and NA antigens can be mixed during manufacture of a vaccine composition (e.g., in dry powder), or dry powder formulations of individual HA and NA antigens can be combined. An antigenic protein can be surface proteins from the pathogen. An antigenic protein can be produced recombinantly. For example, nucleic acid encoding an antigen of interest can be introduced in a prokaryotic cell (e.g. bacteria), eukaryotic cells (e.g., yeast cells and insect cells), and the protein can be expressed and purified from the cells. Where the pathogen is a virus, nonessential components of a virion can be removed (e.g., using ether and detergents).

In some embodiments, a method of generating a vaccine composition (e.g., in dry powder) described herein can be used to produce a virosomal vaccine. A virosomal vaccine comprises virus-like particles of reconstituted virus envelopes with no genetic material of the native virus. Influenza virosomes are vesicles consisting of a unilamellar phospholipid bilayer with intercalated HA and NA proteins. Because they have no genetic material, virosomes are not infectious.

In some embodiments, a concentration of an antigen protein (e.g., antigen or antigen containing component) in a liquid antigen mixture can be from about 0.05 mg/mL to 10 mg/mL, about 0.1 mg/mL to 10 mg/mL, about 0.1 mg/mL to 5 mg/mL, about 0.1 mg/mL to 2.5 mg/mL, about 0.1 mg/mL to 1 mg/mL, about 0.1 mg/mL to 0.5 mg/mL, about 0.5 mg/mL to 1 mg/mL, about 0.05 mg/mL to 1 mg/mL, or about 0.05 mg/mL to 2.5 mg/mL. The concentration of an antigen protein (e.g., antigen or antigen containing component) in a liquid antigen mixture can be about 0.05 mg/mL, 0.1 mg/mL, 0.2 mg/mL, 0.3 mg/mL, 0.4 mg/mL, 0.5 mg/mL, 0.6 mg/mL, 0.7 mg/mL, 0.8 mg/mL, 0.9 mg/mL, 1.0 mg/mL, 1.1 mg/mL, 1.2 mg/mL, 1.3 mg/mL, 1.4 mg/mL, 1.5 mg/mL, 1.6 mg/mL, 1.7 mg/mL, 1.8 mg/mL, 1.9 mg/mL, 2.0 mg/mL, 2.5 mg/mL, 3 mg/mL, 3.5 mg/mL, 4 mg/mL, 4.5 mg/mL, 5 mg/mL, 5.5 mg/mL, 6 mg/mL, 6.5 mg/mL, 7.0 mg/mL, 8.0 mg/mL, 8.5 mg/mL, 9 mg/mL, or 10 mg/mL. The concentration of an antigen protein (e.g. antigen or antigen-containing component) in a liquid antigen mixture can be more than about 0.05 mg/mL, 0.1 mg/mL, 0.2 mg/mL, 0.3 mg/mL, 0.4 mg/mL, 0.5 mg/mL, 0.6 mg/mL, 0.7 mg/mL, 0.8 mg/mL, 0.9 mg/mL, 1.0 mg/mL, 1.1 mg/mL, 1.2 mg/mL, 1.3 mg/mL, 1.4 mg/mL, 1.5 mg/mL, 1.6 mg/mL, 1.7 mg/mL, 1.8 mg/mL, 1.9 mg/mL, 2.0 mg/mL, 2.5 mg/mL, 3 mg/mL, 3.5 mg/mL, 4 mg/mL, 4.5 mg/mL, 5 mg/mL, 5.5 mg/mL, 6 mg/mL, 6.5 mg/mL, 7.0 mg/mL, 8.0 mg/mL, 8.5 mg/mL, 9 mg/mL, or 10 mg/mL.

In some embodiments, a vaccine composition (e.g., in dry powder) can be used to prevent and/or treat infection by one or more influenza viruses. Influenza viruses belong to the Orthomyxoviridae family of viruses, which includes five genera: Influenzavirus A, Influenzavirus B, Influenzavirus C, Isavirus, and Thogotovirus. Dhori virus is a species of the genus Thogotovirus. An influenza virus can infect humans and other species. Influenza type A viruses can infect humans, birds, pigs, horses, seals and other animals. Wild birds can be natural hosts for these viruses. Influenza type A viruses can be divided into subtypes and named on the basis of two proteins on the surface of the virus: hemagglutinin (HA) and neuraminidase (NA). For example, an "H7N2 virus" designates an influenza A subtype that has an HA7 protein and an NA2 protein. Similarly an "H5N1" virus has an HA 5 protein and an NA 1 protein. In some embodiments, disclosed herein are any combinations of HA subtypes and NA subtypes. Any number of the HA subtypes (HAL HA2, HA3, HA4, HA5, HA6, HA7, HA8, HA9, HA10, HA11, HA12, HA13, HA14, HA15, and HA16) can be combined with any number of the NA subtypes (NA1, NA2, NA3, NA4, NA5, NA6, NA7, NA8, and NA9) to produce a vaccine to prevent or treat an infection. The HA and NA subtypes can also be used individually in a vaccine to prevent or treat infection. Different subtype vaccines can be combined at the point of use, either sequentially or simultaneously, to prevent or treat an infection. Some influenza A subtypes (e.g., H1N1, H1N2, and H3N2) are currently in general circulation among people. Other subtypes can be found in other animal species. For example, H7N7 and H3N8 viruses can cause illness in horses, and H3N8 also has recently been shown to cause illness in dogs (http://www.cdc.gov/flu/avian/gen-info/flu-viruses).

In some aspects, antiviral agents can be used to protect high-risk groups (e.g., individuals in a hospital unit, individuals at an institute caring for the elderly, or immunosuppressed individuals). A potential use for an antiviral agent is to limit the spread and severity of the future pandemics whether caused by, e.g. avian H5N1 or another strains of influenza virus (e.g., H1N1). Avian influenza A viruses of the subtypes H5 and H7, including H5N1, H7N7, and H7N3 viruses, have been associated with high pathogenicity, and human infection with these viruses have ranged from mild (e.g., H7N3, H7N7) to severe and fatal disease (e.g., H7N7, H5N1). Human illness due to infection with low pathogenicity viruses has been documented, including very mild symptoms (e.g., conjunctivitis) to influenza-like illness. Examples of low pathogenicity viruses that have infected humans include H7N7, H9N2, and H7N2. (http://www.cdc.gov/flu/avian/gen-info/flu-viruses).

In some embodiments, influenza B viruses can be found in humans and can also infect seals. Unlike influenza A viruses, these viruses are not classified according to subtype. Influenza B viruses can cause morbidity and mortality among humans, but in general are associated with less severe epidemics than influenza A viruses. Although influenza type B viruses can cause human epidemics, they have not caused pandemics. (http://www.cdc.gov/flu/avian/gen-info/flu-viruses).

In some embodiments, influenza type C viruses can cause mild illness in humans and do not cause epidemics or pandemics. These viruses can also infect dogs and pigs. These viruses are not classified according to subtype. (http://www.cdc.gov/flu/avian/gen-info/flu-viruses).

In some embodiments, a methods and composition described herein can be useful for the prevention and/or treatment of infection by any virus, including, for example, Abelson leukemia virus, Abelson murine leukemia virus, Abelson's virus, Acute laryngotracheobronchitis virus, Adelaide River virus, Adeno associated virus group, Adenovirus, African horse sickness virus, African swine fever virus, AIDS virus, Aleutian mink disease parvovirus, Alpharetrovirus, Alphavirus, ALV related virus, Amapari virus, Aphthovirus, Aquareovirus, Arbovirus, Arbovirus C, arbovirus group A, arbovirus group B, Arenavirus group, Argentine hemorrhagic fever virus, Argentine hemorrhagic fever virus, Arterivirus, Astrovirus, Ateline herpesvirus group, Aujezky's disease virus, Aura virus, Ausduk disease virus, Australian bat lyssavirus, Aviadenovirus, avian erythroblastosis virus, avian infectious bronchitis virus, avian leukemia virus, avian leukosis virus, avian lymphomatosis virus, avian myeloblastosis virus, avian paramyxovirus, avian pneumoencephalitis virus, avian reticuloendotheliosis virus, avian sarcoma virus, avian type C retrovirus group, Avihepadnavirus, Avipoxvirus, B virus, B19 virus, Babanki virus, baboon herpesvirus, baculovirus, Barmah Forest virus, Bebaru virus, Berrimah virus, Betaretrovirus, Birnavirus, Bittner virus, BK virus, Black Creek Canal virus, bluetongue virus, Bolivian hemorrhagic fever virus, Boma disease virus, border disease of sheep virus, borna virus, bovine alphaherpesvirus 1, bovine alphaherpesvirus 2, bovine coronavirus, bovine ephemeral fever virus, bovine immunodeficiency virus, bovine leukemia virus, bovine leukosis virus, bovine mammillitis virus, bovine papillomavirus, bovine papular stomatitis virus, bovine parvovirus, bovine syncytial virus, bovine type C oncovirus, bovine viral diarrhea virus, Buggy Creek virus, bullet shaped virus group, Bunyamwera virus supergroup, Bunyavirus, Burkitt's lymphoma virus, Bwamba Fever, CA virus, Calicivirus, California encephalitis virus, camelpox virus, canarypox virus, canid herpesvirus, canine coronavirus, canine distemper virus, canine herpesvirus, canine minute virus, canine parvovirus, Cano Delgadito virus, caprine arthritis virus, caprine encephalitis virus, Caprine Herpes Virus, Capripox virus, Cardiovirus, caviid herpesvirus 1, Cercopithecid herpesvirus 1, cercopithecine herpesvirus 1, Cercopithecine herpesvirus 2, Chandipura virus, Changuinola virus, channel catfish virus, Charleville virus, chickenpox virus, Chikungunya virus, chimpanzee herpesvirus, chub reovirus, chum salmon virus, Cocal virus, Coho salmon reovirus, coital exanthema virus, Colorado tick fever virus, Coltivirus, Columbia SK virus, common cold virus, contagious ecthyma virus, contagious pustular dermatitis virus, Coronavirus, Corriparta virus, coryza virus, cowpox virus, coxsackie virus, CPV (cytoplasmic polyhedrosis virus), cricket paralysis virus, Crimean-Congo hemorrhagic fever virus, croup associated virus, Cryptovirus, Cypovirus, Cytomegalovirus, cytomegalovirus group, cytoplasmic polyhedrosis virus, deer papillomavirus, deltaretrovirus, dengue virus, Densovirus, Dependovirus, Dhori virus, diploma virus, *Drosophila* C virus, duck hepatitis B virus, duck hepatitis virus 1, duck hepatitis virus 2, duovirus, Duvenhage virus, Deformed wing virus DWV, eastern equine encephalitis virus, eastern equine encephalomyelitis virus, EB virus, Ebola virus, Ebola-like virus, echo virus, echovirus, echovirus 10, echovirus 28, echovirus 9, ectromelia virus, EEE virus, EIA virus, EIA virus, encephalitis virus, encephalomyocarditis group virus, encephalomyocarditis virus, Enterovirus, enzyme elevating virus, enzyme elevating virus (LDH), epidemic hemorrhagic fever virus, epizootic hemorrhagic disease virus, Epstein-Barr virus, equid alphaherpesvirus 1, equid alphaherpesvirus 4, equid herpesvirus 2, equine abortion virus, equine arteritis virus, equine encephalosis virus, equine infectious anemia virus, equine morbillivirus, equine rhinopneumonitis virus, equine rhinovirus, Eubenangu virus, European elk papillomavirus, European swine fever virus, Everglades virus, Eyach virus, felid herpesvirus 1, feline calicivirus, feline fibrosarcoma virus, feline herpesvirus, feline immunodeficiency virus, feline infectious peritonitis virus, feline leukemia/sarcoma virus, feline leukemia virus, feline panleukopenia virus, feline parvovirus, feline sarcoma virus, feline syncytial virus, Filovirus, Flanders virus, Flavivirus, foot and mouth disease virus, Fort Morgan virus, Four Corners hantavirus, fowl adenovirus 1, fowlpox virus, Friend virus, Gammaretrovirus, GB hepatitis virus, GB virus, German measles virus, Getah virus, gibbon ape leukemia virus, glandular fever virus, goatpox virus, golden shinner virus, Gonometa virus, goose parvovirus, granulosis virus, Gross' virus, ground squirrel hepatitis B virus, group A arbovirus, Guanarito virus, guinea pig cytomegalovirus, guinea pig type C virus, Hantaan virus, Hantavirus, hard clam reovirus, hare fibroma virus, HCMV (human cytomegalovirus), hemadsorption virus 2, hemagglutinating virus of Japan, hemorrhagic fever virus, hendra virus, Henipaviruses, Hepadnavirus, hepatitis A virus, hepatitis B virus group, hepatitis C virus, hepatitis D virus, hepatitis delta virus, hepatitis E virus, hepatitis F virus, hepatitis G virus, hepatitis nonA nonB virus, hepatitis virus, hepatitis virus (nonhuman), hepatoencephalomyelitis reovirus 3, Hepatovirus, heron hepatitis B virus, herpes B virus, herpes simplex virus, herpes simplex virus 1, herpes simplex virus 2, herpesvirus, herpesvirus 7, Herpesvirus ateles, Herpesvirus hominis, Herpesvirus infection, Herpesvirus saimiri, Herpesvirus suis, Herpesvirus varicellae, Highlands J virus, Hirame rhabdovirus, hog cholera virus, human adenovirus 2, human alphaherpesvirus 1, human alphaherpesvirus 2, human alphaherpesvirus 3, human B lymphotropic virus, human betaherpesvirus 5, human coronavirus, human cytomegalovirus group, human foamy virus, human gammaherpesvirus 4, human gammaherpesvirus 6, human hepatitis A virus, human herpesvirus 1 group, human herpesvirus 2 group, human herpesvirus 3 group, human herpesvirus 4 group, human herpesvirus 6, human herpesvirus 8, human immunodeficiency virus, human immunodeficiency virus 1, human immunodeficiency virus 2, human papillomavirus, human T cell leukemia virus, human T cell leukemia virus I, human T cell leukemia virus II, human T cell leukemia virus III, human T cell lymphoma virus I, human T cell lymphoma virus II, human T cell lymphotropic virus type 1, human T cell lymphotropic virus type 2, human T lymphotropic virus I, human T lymphotropic virus II, human T lymphotropic virus III, Ichnovirus, infantile gastroenteritis virus, infectious bovine rhinotracheitis virus, infectious haematopoietic necrosis virus, infectious pancreatic necrosis virus, influenza virus A, influenza virus B, influenza virus C, influenza virus D, influenza virus pr8, insect iridescent virus, insect virus, iridovirus, Japanese B virus, Japanese encephalitis virus, JC virus, Junin virus, Kaposi's sarcoma-associated herpesvirus, Kemerovo virus, Kilham's rat virus, Klamath virus, Kolongo virus, Korean hemorrhagic fever virus, kumba virus, Kysanur forest disease virus, Kyzylagach virus, La Crosse virus, lactic dehydrogenase elevating virus, lactic dehydrogenase virus, Lagos bat virus, Langur virus, lapine parvovirus, Lassa fever virus, Lassa virus, latent rat virus, LCM virus, Leaky virus, Lentivirus, Leporipoxvirus, leukemia virus, leukovirus, lumpy skin disease virus, lymphadenopathy associated virus, Lymphocryptovirus, lymphocytic choriomeningitis virus, lymphoproliferative virus group, Machupo virus, mad itch virus, mammalian type B oncovirus group, mammalian type B retroviruses, mammalian type C retrovirus group, mammalian type D retroviruses, mammary tumor virus, Mapuera virus, Marburg virus, Marburg-like virus, Mason Pfizer monkey virus, Mastadenovirus, Mayaro virus, ME virus, measles virus, Menangle virus, Mengo virus, Mengovirus, Middelburg virus, milkers nodule virus, mink enteritis virus, minute virus of mice, MLV related virus, MM virus, Mokola virus, Molluscipoxvirus, Molluscum contagiosum virus, monkey B virus, monkeypox virus, Mononegavirales, Morbillivirus, Mount Elgon bat virus, mouse cytomegalovirus, mouse encephalomyelitis virus, mouse hepatitis virus, mouse K virus, mouse leukemia virus, mouse mammary tumor virus, mouse minute virus, mouse pneumonia virus, mouse poliomyelitis virus, mouse polyomavirus, mouse sarcoma virus, mousepox virus, Mozambique virus, Mucambo virus, mucosal disease virus, mumps virus, murid betaherpesvirus 1, murid cytomegalovirus 2, murine cytomegalovirus group, murine encephalomyelitis virus, murine hepatitis virus, murine leukemia virus, murine nodule inducing virus, murine polyomavirus, murine sarcoma virus, Muromegalovirus, Murray Valley encephalitis virus, myxoma virus, Myxovirus, Myxovirus multiforme, Myxovirus parotitidis, Nairobi sheep disease virus, Nairovirus, Nanirnavirus, Nariva virus, Ndumo virus, Neethling virus, Nelson Bay virus, neurotropic virus, New World Arenavirus, newborn pneumonitis virus, Newcastle disease virus, Nipah virus, noncytopathogenic virus, Norwalk virus, nuclear polyhedrosis virus (NPV), nipple neck virus, O'nyong'nyong virus, Ockelbo virus, oncogenic virus, oncogenic viruslike particle, oncornavirus, Orbivirus, Orf virus, Oropouche virus, Orthohepadnavirus, Orthomyxovirus, Orthopoxvirus, Orthoreovirus, Orungo, ovine papillomavirus, ovine catarrhal fever virus, owl monkey herpesvirus, Palyam virus, Papillomavirus, Papillomavirus sylvilagi, Papovavirus, parainfluenza virus, parainfluenza virus type 1, parainfluenza virus type 2, parainfluenza virus type 3, parainfluenza virus type 4, Paramyxovirus, Parapoxvirus, paravaccinia virus, Parvovirus, Parvovirus B19, parvovirus group, Pestivirus, Phlebovirus, phocine distemper virus, Picodnavirus, Picornavirus, pig cytomegalovirus—pigeonpox virus, Piry virus, Pixuna virus, pneumonia virus of mice, Pneumovirus, poliomyelitis virus, poliovirus, Polydnavirus, polyhedral virus, polyoma virus, Polyomavirus, Polyomavirus bovis, Polyomavirus cercopi theci, Polyomavirus hominis 2, Polyomavirus maccacae 1, Polyomavirus muris 1, Polyomavirus muris 2, Polyomavirus papionis 1, Polyomavirus papionis 2, Polyomavirus sylvilagi, Pongine herpesvirus 1, porcine epidemic diarrhea virus, porcine hemagglutinating encephalomyelitis virus, porcine parvovirus, porcine transmissible gastroenteritis virus, porcine type C virus, pox virus, poxvirus, poxvirus variolae, Prospect Hill virus, Provirus, pseudocowpox virus, pseudorabies virus, psittacinepox virus, quailpox virus, rabbit fibroma virus, rabbit kidney vaculolating virus, rabbit papillomavirus, rabies virus, raccoon parvovirus, raccoonpox virus, Ranikhet virus, rat cytomegalovirus, rat parvovirus, rat virus, Rauscher's virus, recombinant vaccinia virus, recombinant virus, reovirus, reovirus 1, reovirus 2, reovirus 3, reptilian type C virus, respiratory infection virus, respiratory syncytial virus, respiratory virus, reticuloendotheliosis virus, Rhabdovirus, Rhabdovirus carpia, Rhadinovirus, Rhinovirus, Rhizidiovirus, Rift Valley fever virus, Riley's virus, rinderpest virus, RNA tumor virus, Ross River virus, Rotavirus, rougeole virus, Rous sarcoma virus, rubella virus, rubeola virus, Rubivirus, Russian autumn encephalitis virus, SA 11 simian virus, SA2 virus, Sabia virus, Sagiyama virus, Saimirine herpesvirus 1, salivary gland virus, sandfly fever virus group, Sandjimba virus, SARS virus, SDAV (sialodacryoadenitis virus), sealpox virus, Semliki Forest Virus, Seoul virus, sheeppox virus, Shope fibroma virus, Shope papilloma virus, simian foamy virus, simian hepatitis A virus, simian human immunodeficiency virus, simian immunodeficiency virus, simian parainfluenza virus, simian T cell lymphotrophic virus, simian virus, simian virus 40, Simplexvirus, Sin Nombre virus, Sindbis virus, smallpox virus, South American hemorrhagic fever viruses, sparrowpox virus, Spumavirus, squirrel fibroma virus, squirrel monkey retrovirus, SSV 1 virus group, STLV (simian T lymphotropic virus) type I, STLV (simian T lymphotropic virus) type II, STLV (simian T lymphotropic virus) type III, stomatitis papulosa virus, submaxillary virus, suid alphaherpesvirus 1, suid herpesvirus 2, Suipoxvirus, swamp fever virus, swinepox virus, Swiss mouse leukemia virus, TAC virus, Tacaribe complex virus, Tacaribe virus, Tanapox virus, Taterapox virus, Tench reovirus, Theiler's encephalomyelitis virus, Theiler's virus, Thogoto virus, Thottapalayam virus, Tick borne encephalitis virus, Tioman virus, Togavirus, Torovirus, tumor virus, Tupaia virus, turkey rhinotracheitis virus, turkeypox virus, type C retroviruses, type D oncovirus, type D retrovirus group, ulcerative disease rhabdovirus, Una virus, Uukuniemi virus group, vaccinia virus, vacuolating virus, varicella zoster virus, Varicellovirus, Varicola virus, variola major virus, variola virus, Vasin Gishu disease virus, VEE virus, Venezuelan equine encephalitis virus, Venezuelan equine encephalomyelitis virus, Venezuelan hemorrhagic fever virus, vesicular stomatitis virus, Vesiculovirus, Vilyuisk virus, viper retrovirus, viral haemorrhagic septicemia virus, Visna Maedi virus, Visna virus, volepox virus, VSV (vesicular stomatitis virus), Wallal virus, Warrego virus, wart virus, WEE virus, West Nile virus, western equine encephalitis virus, western equine encephalomyelitis virus, Whataroa virus, Winter Vomiting Virus, woodchuck hepatitis B virus, woolly monkey sarcoma virus, wound tumor virus, WRSV virus, Yaba monkey tumor virus, Yaba virus, Yatapoxvirus, yellow fever virus, and the Yug Bogdanovac virus.

In some embodiments, a composition disclosed herein comprises an antigen that is a DNA or RNA of any protein antigen (e.g., virus) disclosed herein.

B. Other Components

In some aspects, the present disclosure provides methods for preparing a vaccine which can preserve some or all of a three-dimensional configuration of the antigenic component (e.g., virus, protein). Thus, the methods provided herein can allow for the production of vaccines in which the antigenic determinants on the pathogen or component thereof are preserved in an intact state. For example, retaining three-dimensional structure of a protein in a vaccine can allow for retention of "conformational" epitopes to which an immune response can be triggered. "Conformational" epitopes are those which rely upon protein folding and generally are not comprised entirely of amino acids in linear form. Furthermore, the methods provided herein to produce vaccines can result in retention of antigenic potency (e.g., the ability to induce an immune response), such that the level of immune response in a reaction to a given amount of vaccine is at least about 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, or 50% as compared to exposure to the pathogen or other naturally-occurring antigenic source. Additionally, the methods provided herein can allow for the production of a vaccine in which a particular antigen retains high levels of antigenic potency (e.g., at least about 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, or 50%) of the total antigenic protein subjected to the freeze-drying methods described herein.

In some aspects, components of a liquid antigen mixture can be chosen to perform certain functions. For example, one component can be utilized to provide stability to the antigen for which the vaccine is being developed. Primarily, such components can prevent antigenic degradation during the subsequent freeze-drying process. These components can comprise any stabilizing molecule or compound, for example sugars, amino acids and/or polymers. Typically, an antigenic stabilizing agent will be wholly or partially water soluble.

In some embodiments, suitable antigenic stabilizers will not produce cake characteristics undesired to prepare vaccine compositions (e.g., in dry powder) for mucosal delivery, e.g., shrinkage (e.g., concave), cracking, collapse or melt-back, and insufficiently dry, hard cake not to result in fine powder, and low moisture resistance in the processes described herein. Exemplary sugars which can be utilized to produce a liquid antigen mixture include trehalose, mannitol, inulin, sucrose, pullulan and/or the like. Exemplary amino acids which can be utilized, include, but are not limited to isoleucine, valine, leucine, arginine, asparagine, glutamine, glycine, histidine, glutamate and lysine. An exemplary polymer is polyethylene glycol (PEG), but other polymers that can be utilized can include dextran, human serum albumin (HSA), nonhydrolyzed gelatin, methylcellulose, xanthan gum, carrageenan, collagen, chondroitin sulfate, a sialylated polysaccharide, actin, myosin, microtubules, dynein, kinetin, polyvinyl pyrrolidone, hydrolyzed gelatin, and/or the like. A surfactant can be, e.g., a polyethylene glycol, sorbitan monolaurate (Tween 20), a polyoxyethylenesorbitan monooleate (Tween 80), a block copolymer of polyethylene and polypropylene glycol (Pluronic), and/or the like.

In some embodiments, a use of one or more of these stabilizers in the present methods can result in a freeze-dried antigen that does form fine particle and low hygroscopic powder. For example, a freeze-dried antigen having large sized particles with hard cake which is difficult to apply to the mucosal delivery compositions is produced when a general freeze-drying method is applied (Non-Patent Publication #1). Furthermore, although other technology with a use of trehalose as an antigen-protectant provided the freeze-dried antigen having fine sized particles which is easy to apply to the mucosal delivery compositions is produced when the freeze-drying method with the quick freezing step is applied (Patent Publication #2), a moisture resistance of the freeze-dried antigen provided from the technology is not sufficient due to hygroscopic form of trehalose although the moisture resistance is critical to keep powder form which is needed to be delivered from a mucosal delivery device and to retain antigenic potency until delivering to a subject.

In some embodiments, provided herein is a method that the liquid antigen mixture containing the first saccharide (selected from trehalose, inulin, sucrose, maltose, isomaltose, maltotriose pullulan or raffinose) which are in amorphous form as an antigen-protectant, the second saccharide (selected from mannitol, sorbitol, glucose or galactose) which is both in amorphous and crystal forms as an antigen-protectant and an agent to increase moisture resistance, and phosphate buffer saline, is freeze-dried with an annealing step to formulate at least 20% (w/w) of the second saccharide in crystal form. Such methods can lead to the production of freeze-dried antigen with cake characteristics desired for vaccine composition (e.g., in dry powder) for mucosal delivery, e.g., neither shrinkage, cracking, collapse nor melt-back, and sufficiently dry, easily friable cake to result in fine powder, and adequate moisture resistance as well as high antigenic potency. Furthermore, this method does not need an additional step such as a quick freezing which is operated outside of a freeze-drying equipment.

In some embodiments, per 1 mL of liquid antigen mixture, a first saccharide can be added, for example, about 1 mg to 250 mg, about 5 mg to 250 mg, about 5 mg to 150 mg, about 5 mg to 100 mg, about 10 mg to 100 mg, about 10 mg to 75 mg, about 5 mg to 75 mg or about 10 mg to 50 mg. The first saccharide can be added about 1 mg, 2.5 mg, 5 mg, 7.5 mg/mL, 10 mg, 12.5 mg, 15 mg, 20 mg, 25 mg, 30 mg, 35 mg, 45 mg, 50 mg, 60 mg, 80 mg, 100 mg, 150 mg, 200 mg, or 250 mg per 1 mL of liquid antigen mixture.

In some embodiments, a second saccharide can be added at a ratio of the second saccharide to the first saccharide, for example, about 1:0.8, 1:0.9, 1:1, 1:1.1, 1:1.2, 1:1.3, 1:1.4, 1:1.5, 1:1.6, 1:1.7, 1:1.8, 1:1.9, 1:2, 1:21, 1:22, 1:23, 1:24, 1:25, 1:26, 1:27, 1:28, 1:29, or 1:3.

In some embodiments, a liquid antigen mixture to be used for the freeze-drying can comprise one or more pH buffers. The pH buffer can be, e.g., potassium phosphate, sodium phosphate, disodium hydrogenphosphate, potassium dihydrogenphosphate, sodium hydroxide, sodium acetate, histidine, HEPES, ACES, ADA, ADA, disodium salt, ADA monosodium salt, AMPSO, 2-aminoethanol, 2-amino-2-methyl-1,3-propanediol, 2-amino-2-methyl-1-propanol, 3-amino-1-propanesulfonic acid sodium salt, BES, bicine, Bis-Tris, Bis-Tris HCl, Bis-Tris propane, CAPS, CAPSO, CHES, DIPSO, DIPSO sodium salt, glycinamide HCl, glycine, HEPPS, HEPPSO, IVIES, MOPS, MOPSO, PIPES, TAPS, TAPSO, TES, tricine, triethanolamine, imidazole, sodium citrate, sodium succinate, ammonium bicarbonate, and/or a carbonate. A buffer can be phosphate buffered saline. The pH can be maintained at between about pH 3 to about pH 8, about pH 4 to 8, about pH 5 to 8, about pH 6 to 8, or about pH 6.0, 61, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, or 8.0. The salt concentration of the buffer can be from to about 0.25% to about 3% (w/w). A liquid antigen mixture can comprise, consist essentially of, or consist of one or more antigens, two or more saccharides and one or more buffers. A liquid antigen mixture can comprise, consist essentially of, or consist of one or more antigens, one or more antigen-protectant, one or more agent to increase moisture resistance and one or more buffers.

In some embodiments, a liquid antigen mixture used to generate a vaccine composition (e.g., in dry powder) by the methods described herein can contain one or more other drugs, bulking agents, and/or sustained release polymers. Other drugs useful in the compositions disclosed herein, can include, e.g., aids to penetration, decongestants, bronchiole relaxers, expectorants, analgesics, and the like. Bulking agents can include, e.g., lactose, mannitol, and/or hydroxyethyl starch (HES). Sustained release semi-permeable polymer matrix of the compositions can include, e.g., polylactides, copolymers of L-glutamic acid and gamma-ethyl-L-glutamate, poly(2-hydroxyethyl methacrylate, or liposomes.

In some embodiments, a vaccine described herein can be made without including an adjuvant. Thus, the final vaccine can be produced using only the pathogen/antigen, a stabilizer, an agent to increase moisture resistance, and a buffer which is then freeze-dried. Following freeze-drying, the vaccine can be combined with a carrier without the need to add an adjuvant prior to producing the final vaccine product. Alternately, the formulation can comprise adjuvant, a substance added to a vaccine to improve the immune response of the vaccine. An adjuvant can be added prior to, or after, freeze drying. Examples of adjuvant include mineral salts, e.g., aluminum hydroxide and aluminum or calcium phosphate gels, oil emulsions and surfactant based formulations, e.g., MF59 (microfluidised detergent stabilized oil-in-water emulsion), QS21 (purified saponin), AS02 ([SBAS2] (oil-in-water+MPL+WS-21)), Montanide ISA-51 and ISA-720 (stabilised water-in-oil emulsion); particulate adjuvants, (e.g., virosomes (unilamellar liposomal vehicles incorporating influenza hemagglutinin), AS04 ([SBAS4] Al salt with MPL), ISCOMS (structured complex of saponins and lipids), polylactide co-glycolide (PLG); microbial derivatives (natural and synthetic), e.g., monophosphoryl lipid A (MPL), Detox (MPL+*M. Phlei* cell wall skeleton), AGP [RC-529] (synthetic acylated monosaccharide), DC_Chol (lipoidal immunostimulators able to self organise into liposomes), OM-174 (lipid A derivative), CpG motifs (synthetic oligonucleotides containing immunostimulatory CpG motifs), modified LT and CT (genetically modified bacterial toxins to provide non-toxic adjuvant effects); endogenous human immunomodulators, e.g., hGM-CSF or hIL-12 (cytokines that can be administered either as protein or plasmid encoded), Immudaptin (C3d tandem array); inert vehicles, such as gold particles; and squalene. The liquid antigen mixture and the final vaccine composition (e.g., in dry powder) can have no adjuvant.

In some aspects, a composition disclosed herein comprises one or more pharmaceutically acceptable excipients. Exemplary pharmaceutically acceptable excipients for the purposes of pharmaceutical compositions disclosed herein include, but are not limited to, binders, disintegrants, superdisintegrants, lubricants, diluents, fillers, flavors, glidants, sorbents, solubilizers, chelating agents, emulsifiers, thickening agents, dispersants, stabilizers, suspending agents, adsorbents, granulating agents, preservatives, buffers, coloring agents and sweeteners or combinations thereof. Examples of binders include microcrystalline cellulose, hydroxypropyl methylcellulose, carboxyvinyl polymer, polyvinylpyrrolidone, polyvinylpolypyrrolidone, carboxymethylcellulose calcium, carboxymethylcellulose sodium, ceratonia, chitosan, cottonseed oil, dextrates, dextrin, ethylcellulose, gelatin, glucose, glyceryl behenate, galactomannan polysaccharide, hydroxyethyl cellulose, hydroxyethylmethyl cellulose, hydroxypropyl cellulose, hypromellose, inulin, lactose, magnesium aluminum silicate, maltodextrin, methylcellulose, poloxamer, polycarbophil, polydextrose, polyethylene glycol, polyethylene oxide, polymethacrylates, sodium alginate, sorbitol, starch, sucrose, sunflower oil, vegetable oil, tocofersolan, zein, or combinations thereof. Examples of disintegrants include croscarmellose sodium, sodium starch glycolate, lactose, magnesium aluminum silicate, methylcellulose, polacrilin potassium, sodium alginate, starch, or combinations thereof. Examples of a lubricant include stearic acid, sodium stearyl fumarate, glyceryl behenate, calcium stearate, glycerin monostearate, glyceryl palmitostearate, magnesium lauryl sulfate, mineral oil, palmitic acid, myristic acid, poloxamer, polyethylene glycol, sodium benzoate, sodium chloride, sodium lauryl sulfate, talc, zinc stearate, potassium benzoate, magnesium stearate or combinations thereof. Examples of diluents include talc, ammonium alginate, calcium carbonate, calcium lactate, calcium phosphate, calcium silicate, calcium sulfate, cellulose, cellulose acetate, corn starch, dextrates, dextrin, dextrose, erythritol, ethylcellulose, fructose, fumaric acid, glyceryl palmitostearate, isomalt, kaolin, lactitol, lactose, magnesium carbonate, magnesium oxide, maltodextrin, maltose, mannitol, microcrystalline cellulose, polydextrose, polymethacrylates, simethicone, sodium alginate, sodium chloride, sorbitol, starch, sucrose, sulfobutylether beta-cyclodextrin, tragacanth, trehalose, xylitol, or combinations thereof.

III. Freeze Drying Method to Generate Freeze-Dried Antigen

In some aspects, a liquid antigen mixture can be converted to a powder by freeze drying method. Freeze-drying, also known as lyophilization, works by freezing the material and then reducing the surrounding pressure to allow the frozen water in the material to sublimate directly from the solid phase to the gas phase. In some embodiments, a freeze-drying method disclosed herein can comprise a freezing step with annealing and a drying step.

A. Freezing Step with Annealing

In some aspects, a liquid antigen mixture freezes for definite period of time on the tray pre-cooled in a freeze-drying equipment.

In some embodiments, a pre-cool temperature can occur at, for example, at about −50 degrees C., −45 degrees C., −40 degrees C., −35 degrees C., −30 degrees C., −25 degrees C., −20 degrees C., −15 degrees C., or −10 degrees C. The pre-cool temperature can occur at, for example, at less than about −50 degrees C., −45 degrees C., −40 degrees C., −35 degrees C., −30 degrees C., −25 degrees C., −20 degrees C., −15 degrees C., or −10 degrees C. The pre-cool temperature can occur at, e.g., at about −50 degrees C. to −10 degrees C., about −40 degrees C. to −20 degrees C., or about −35 degrees C. to −25 degrees C.

In some embodiments, a liquid antigen mixture can leave at the pre-cooled temperature set for, for example, for about 1 hour, 1.5 hours, 2 hours, 3 hours, 4 hours, 5 hours, 6 hours, 12 hours, or 24 hours. The liquid antigen mixture can leave at the pre-cooled temperature set for, for example, for more than 1 hour, 1.5 hours, 2 hours, 3 hours, 4 hours, 5 hours, 6 hours, 12 hours, or 24 hours. The liquid antigen mixture can leave at the pre-cooled temperature set for, for example, for 1 to 24 hours, 1 to 12 hours, 1 to 6 hours, 1.5 to 6 hours, or 1.5 to 3 hours.

In some embodiments, after the first freezing, the frozen liquid antigen mixture can be annealed to form at least 20% (w/w) of the second saccharide in crystal form. The freeze-drying method with mannitol-trehalose-sodium chloride-based formulation to increase a moisture resistance of freeze-dried powder was provided (Non-Patent Publication #3). In this prior technology, a major portion of mannitol is formed in crystal form by means of annealing step to increase moisture resistance. In some embodiments, a small portion, for example, at least 20% of the second saccharide is formed in crystal form by annealing to minimize the deactivation of antigenic potency by the crystal form. The second saccharide with crystal form can be, for example, more than 20, 30, 40, 50, 60, 70 or 80% (w/w) of the second saccharide added in the liquid antigen mixture.

In some embodiments, the annealing temperature can occur at, for example, at about −28 degrees C., −27 degrees C., −26 degrees C., −25 degrees C., −24 degrees C., −23 degrees C., −22 degrees C., −21 degrees C., −20 degrees C., −19 degrees C., or −18 degrees C. The annealing temperature can occur at, for example, at about −28 to −18 degrees C., about −25 degrees C. to −20 degrees C., or about −24 degrees C. to −22 degrees C. The frozen antigen mixture can leave at the annealing temperature set for, for example, for about 1 hour, 2 hours, 3 hours, 4 hours, 5 hours, 6 hours, 12 hours, or 24 hours. The frozen antigen mixture can leave at the annealing temperature set for, for example, for more than 1 hour, 2 hours, 3 hours, 4 hours, 5 hours, 6 hours, 12 hours, or 24 hours. The frozen antigen mixture can leave at the annealing temperature set for, for example, for 1 to 24 hours, 1 to 12 hours, or 2 to 6 hours. The annealing can conduct after the second freezing step again.

In some embodiments, after the annealing, the frozen liquid antigen mixture can be frozen in the freeze-drying equipment again. The second freezing temperature can occur at, for example, at about −50 degrees C., −45 degrees C., −40 degrees C., −35 degrees C., −30 degrees C., −25 degrees C., or −20 degrees C. The second freezing temperature can occur at, for example, at less than about −50 degrees C., −45 degrees C., −40 degrees C., −35 degrees C., −30 degrees C., −25 degrees C., or −20 degrees C. The second freezing temperature can occur at, for example, at about −50 degrees C. to −20 degrees C., about −50 degrees C. to −30 degrees C., or about −50 degrees C. to −40 degrees C.

The frozen antigen mixture can leave at the second freezing temperature set for, for example, for about 1 hour, 1.5 hours, 2 hours, 3 hours, 4 hours, 5 hours, 6 hours, 12 hours, or 24 hours. The liquid antigen mixture can leave at the pre-cooled temperature set for, for example, for more than 1 hour, 1.5 hours, 2 hours, 3 hours, 4 hours, 5 hours, 6 hours, 12 hours, or 24 hours. The liquid antigen mixture can leave at the pre-cooled temperature set for, for example, for 1 to 24 hours, 1 to 12 hours, 1 to 6 hours, 1.5 to 6 hours, or 1.5 to 3 hours.

B. Drying Step

In some aspects, after second freezing, the frozen antigen mixture can be dried in the freeze-drying equipment. Drying can occur in one or more steps (e.g., different temperatures at the same pressure).

In some embodiments, a primary drying (first drying) can occur at, for example, at about −45 degrees C., −40 degrees C., −35 degrees C., −30 degrees C., −25 degrees C., −20 degrees C., −15 degrees C., or −10 degrees C. The primary drying can occur at, for example, at about −45 degrees C. to −10 degrees C., about −45 degrees C. to −20 degrees C., or about −45 degrees C. to −30 degrees C.

In some embodiments, a primary drying (first drying) can be, for example, about 10 mtorr to 300 mtorr, about 25 mtorr to 300 mtorr, about 50 mtorr to 250 mtorr, or about 50 mtorr to 200 mtorr. The freeze-drying can occur at about 10 mtorr, 20 mtorr, 30 mtorr, 40 mtorr, 50 mtorr, 60 mtorr, 70 mtorr, 80 mtorr, 90 mtorr, 100, mtorr, 110 mtorr, 120 mtorr, 130 mtorr, 140 mtorr, 150 mtorr, 160 mtorr, 170 mtorr, 180 mtorr, 190 mtorr, 200 mtorr, 210 mtorr, 220 mtorr, 230 mtorr, 240 mtorr, 250 mtorr, 260 mtorr, 270 mtorr, 280 mtorr, 290 mtorr, or 300 mtorr. Freeze-drying can occur at more than about 10 mtorr, 20 mtorr, 30 mtorr, 40 mtorr, 50 mtorr, 60 mtorr, 70 mtorr, 80 mtorr, 90 mtorr, 100, mtorr, 110 mtorr, 120 mtorr, 130 mtorr, 140 mtorr, 150 mtorr, 160 mtorr, 170 mtorr, 180 mtorr, 190 mtorr, 200 mtorr, 210 mtorr, 220 mtorr, 230 mtorr, 240 mtorr, 250 mtorr, 260 mtorr, 270 mtorr, 280 mtorr, 290 mtorr, or 300 mtorr.

In some embodiments, a duration of a primary drying (first drying) can be, for example, from about 4 hr to 96 hr, about 6 hr to 96 hr, about 12 hr to 96 hr, about 24 hr to 96 hr, about 48 hr to 96 hr, or about 48 hr to 72 hr. The duration of the primary drying can be, for example, for more than 6 hr, more than 8 hr, more than 12 hr, more than 18 hr, more than 24 hr, more than 36 hr, more than 48 hr, more than 72 hr, or more than 96 hr.

In some embodiments, after a primary drying, a second drying can occur at, for example, at about −10 degrees C., −5 degrees C., 0 degrees C., 5 degrees C., 10 degrees C., 15 degrees C., 20 degrees C., 25 degrees C., 30 degrees C., 35 degrees C., or 40 degrees C. The primary drying can occur at, for example, at about −10 degrees C. to 40 degrees C., about 0 degrees C. to 40 degrees C., or about 10 degrees C. to 35 degrees C.

In some embodiments, a secondary drying can be, for example, about 10 mtorr to 300 mtorr, about 25 mtorr to 300 mtorr, about 50 mtorr to 250 mtorr, or about 50 mtorr to 200 mtorr. The freeze-drying can occur at about 10 mtorr, 20 mtorr, 30 mtorr, 40 mtorr, 50 mtorr, 60 mtorr, 70 mtorr, 80 mtorr, 90 mtorr, 100, mtorr, 110 mtorr, 120 mtorr, 130 mtorr, 140 mtorr, 150 mtorr, 160 mtorr, 170 mtorr, 180 mtorr, 190 mtorr, 200 mtorr, 210 mtorr, 220 mtorr, 230 mtorr, 240 mtorr, 250 mtorr, 260 mtorr, 270 mtorr, 280 mtorr, 290 mtorr, or 300 mtorr. Freeze-drying can occur at more than about 10 mtorr, 20 mtorr, 30 mtorr, 40 mtorr, 50 mtorr, 60 mtorr, 70 mtorr, 80 mtorr, 90 mtorr, 100, mtorr, 110 mtorr, 120 mtorr, 130 mtorr, 140 mtorr, 150 mtorr, 160 mtorr, 170 mtorr, 180 mtorr, 190 mtorr, 200 mtorr, 210 mtorr, 220 mtorr, 230 mtorr, 240 mtorr, 250 mtorr, 260 mtorr, 270 mtorr, 280 mtorr, 290 mtorr, or 300 mtorr.

In some embodiments, a duration of a secondary drying can be, for example, from about 1 hr to 12 hr, about 2 hr to 12 hr, about 2 hr to 12 hr, about 3 hr to 12 hr, about 3 hr to 10 hr, or about 3 hr to 8 hr. The duration of the secondary drying can be, for example, for more than 1 hr, more than 2 hr, more than 3 hr, more than 4 hr, more than 6 hr, more than 8 hr, more than 10 hr, more than 12 hr, or more than 24 hr.

In some embodiments, after freeze drying, a vaccine composition (e.g., in dry powder) packaged in an airtight container can be stored (preserved) at a temperature of about 4 to 25 degrees C. The relative humidity of the preservation condition can be about 0% to 70%, about 0% to 60%, about 0% to 50%, about 0% to 40%, about 0% to 30%, about 0% to 20%, about 0% to 10%, or about 0% to 5%. The relative humidity of the preservation can be less than about 80%, 75%, 70%, 65%, 60%, 55%, 50%, 45%, 40%, 35%, 30%, 25%, 24%, 23%, 22%, 21%, 60%, 19%, 18%, 17%, 16%, 15%, 14%, 13%, 12%, 11%, 10%, 9%, 8%, 7%, 6%, 5%, 4%, 3%, 2%, or 1%.

In some embodiments, a water content of a composition or freeze-dried antigen herein can be about 10%, 9%, 8%, 7%, 6%, 5%, 4%, 3%, 2%, 1%, 0.5%, or 0.1%. In some embodiments, a water content of a composition or freeze-dried antigen can be less than 10%, 9%, 8%, 7%, 6%, 5%, 4%, 3%, 2%, 1%, 0.5%, 0.1%, or 0.01%.

IV. Carriers/Excipients

In some aspects, a freeze-dried antigen produced by the freeze drying methods described herein can be blended with one or more additional excipients to generate a vaccine composition (e.g., in dry powder). Such excipients include pharmaceutically acceptable excipients, for example, excipients to increase moisture resistance, increase flowability, help to be uniformly and widely delivered from a mucosal delivery device, and prolong a retention time of the antigen on the mucosa. Suitable excipients can be physiologically acceptable water-insoluble and non-gel forming substances such as microcrystalline cellulose. Microcrystalline cellulose can be a specific microcrystalline cellulose that has a specific surface area of at least 1.3 $m^2/g$ and a mean particle size of less than 100 microns. Although any microcrystalline cellulose can be utilized, in some embodiments, the microcrystalline cellulose used to produce the vaccines of the present application can be CEOLUS (registered trademark) PH-F20JP or AVICEL (registered trademark) PH-105.

In some embodiments, an average particle size of the microcrystalline cellulose can be measured by sifting, sieving or laser diffraction. The average particle size of the carrier (e.g., microcrystalline cellulose) can be about: 10 microns, 11 microns, 12 microns, 13 microns, 14 microns, 15 microns, 16 microns, 17 microns, 18 microns, 19 microns, 20 microns, 21 microns, 22 microns, 23 microns, 24 microns, 25 microns, 26 microns, 27 microns, 28 microns, 29 microns, 30 microns, 31 microns, 32 microns, 33 microns, 34 microns, 35 microns, 36 microns, 37 microns, 38 microns, 39 microns, 40 microns, 41 microns, 42 microns, 43 microns, 44 microns, 45 microns, 46 microns, 47 microns, 48 microns, 49 microns, or 50 microns. In some embodiments, microcrystalline cellulose used as a carrier for the vaccine compositions (e.g., in dry powder) described herein can have an average particle size of between 18 microns and 50 microns, measured by, for example, laser diffraction, sieving or sifting.

In some embodiments, a carrier (e.g., microcrystalline cellulose) can be prepared to be of useful particle size distribution. Preparations of carrier can have a particle size distribution of, for example 5-150 microns, 5-100 microns, 5-75 microns, 10-50 microns, or any included sub-ranges of particle size distribution. In a particular embodiment, the carrier can have a particle size distribution of 5-150 microns, a particle size distribution of 5-100 microns, or a particle size distribution of 5-75 microns.

In some aspects, an average particle size of a composition herein can be measured by sifting, sieving or laser diffraction. In some embodiments, the average particle size of the composition can be about: 10 microns, 11 microns, 12 microns, 13 microns, 14 microns, 15 microns, 16 microns, 17 microns, 18 microns, 19 microns, 20 microns, 21 microns, 22 microns, 23 microns, 24 microns, 25 microns, 26 microns, 27 microns, 28 microns, 29 microns, 30 microns, 31 microns, 32 microns, 33 microns, 34 microns, 35 microns, 36 microns, 37 microns, 38 microns, 39 microns, 40 microns, 41 microns, 42 microns, 43 microns, 44 microns, 45 microns, 46 microns, 47 microns, 48 microns, 49 microns, or 50 microns. In some embodiments, a composition herein can have a particle size distribution of about: 5-150 microns, 5-100 microns, 5-75 microns, 10-150 microns, 10-100 microns, 10-75 microns, 10-50 microns, 10-30 microns, or any included sub-ranges of particle size distribution. In some embodiments, a composition can have a particle size distribution of less than 10 microns. In some embodiments, a composition can have a particle size distribution of more than 10 microns. In some embodiments, an average particle size of a composition or carrier (e.g., microcrystalline cellulose) can be about: 51 micro m, 52 micro m, 53 micro m, 54 micro m, 55 micro m, 56 micro m, 57 micro m, 58 micro m, 59 micro m, 60 micro m, 61 micro m, 62 micro m, 63 micro m, 64 micro m, 65 micro m, 66 micro m, 67 micro m, 68 micro m, 69 micro m, 70 micro m, 71 micro m, 72 micro m, 73 micro m, 74 micro m, 75 micro m, 76 micro m, 77 micro m, 78 micro m, 79 micro m, 80 micro m, 81 micro m, 82 micro m, 83 micro m, 84 micro m, 85 micro m, 86 micro m, 87 micro m, 88 micro m, 89 micro m, 90 micro m, 91 micro m, 92 micro m, 93 micro m, 94 micro m, 95 micro m, 96 micro m, 97 micro m, 98 micro m, 99 micro m, 100 micro m, 110 micro m, 120 micro m, 130 micro m, 140 micro m, 150 micro m, 160 micro m, 170 micro m, 180 micro m, 190 micro m, or 200 micro m. In some embodiments, a composition or carrier (e.g., microcrystalline cellulose) described herein can have an average particle size of 25 micro m, 39 micro m, or 57 micro m. In some embodiments, a composition or carrier (e.g., microcrystalline cellulose) described herein can have a particle size distribution of about: 10-200 micro m, 20-200 micro m, 30-200 micro m, 40-200 micro m, 50-200 micro m, 60-200 micro m, 70-200 micro m, 80-200 micro m, 90-200 micro m, 100-200 micro m, 110-200 micro m, 120-200 micro m, 130-200 micro m, 140-200 micro m, 150-200 micro m, 160-200 micro m, 170-200 micro m, 180-200 micro m, 190-200 micro m, or any included sub-ranges of particle size distribution. Powders described herein can have a particle size additional particle size distributions, for example 10-100 micro m, 20-100 micro m, 30-100 micro m, 40-100 micro m, 50-100 micro m, 60-100 micro m, 70-100 micro m, 80-100 micro m, 90-100 micro m, 10-50 micro m, 10-60 micro M, 20-60 micro m, 30-70 micro m, 40-80 micro m, 50-90 micro m, 60-100 micro m, 70-110 micro m, 80-120 micro m, 90-130 micro m, 100-140 micro m, 110-150 micro m, 120-160 micro m, 130-170 micro m, 140-180 micro m, 150-190 micro m, 160-200 micro m, or any included sub-range of particle sizes. The carrier and/or vaccine can have a particle size distribution of, for example, 10-50 micro m, 11-50 micro m, 12-50 micro m, 13-50 micro m, 14-50 micro m, 15-50 micro m, 16-50 micro m, 17-50 micro m, 18-50 micro m, 19-50 micro m, 20-50 micro m., 21-50 micro m, 22-50 micro m, 23-50 micro m, 24-50 micro m, 25-50 micro m, 26-50 micro m, 27-50 micro m, 28-50 micro m, 29-50 micro m, 30-50 micro m, or any included sub-range of particle sizes. In some embodiments, a composition or carrier (e.g., microcrystalline cellulose) described herein can have a particle size distribution of 19-60 micro m, or a particle size distribution of 19-50 micro m. In some embodiments, a composition or carrier (e.g., microcrystalline cellulose) described herein can have an average particle size of less than about 10 micro m, less than about 20 micro m, less than about 30 micro m, less than about 40 micro m, less than about 50 micro m, less than about 60 micro m, less than about 70 micro m, less than about 80 micro m, less than about 90 micro m, less than about 100 micro m and/or minimize particles that are greater than about 20 micro m, greater than about 30 micro m, greater than about 40 micro m, greater than about 50 micro m, greater than about 60 micro m, greater than about 70 micro m, greater than about 80 micro m, greater than about 90 micro m, greater than about 100 micro m, greater than about 110 micro m, greater than about 120 micro m, greater than about 130 micro m, greater than about 140 micro m, greater than about 150 micro m, greater than about 160 micro m, greater than about 170 micro m, greater than about 180 micro m, greater than about 190 micro m, or greater than about 200 micro m.

In some embodiments, a specific surface area of the carrier (e.g., microcrystalline cellulose) is, 1.3 $m^2/g$, 1.4 $m^2/g$, 1.5 $m^2/g$, 1.6 $m^2/g$, 1.7 $m^2/g$, 1.8 $m^2/g$, 1.9 $m^2/g$, 2.0 $m^2/g$, 2.1 $m^2/g$, 2.2 $m^2/g$, 2.3 $m^2/g$, 2.4 $m^2/g$, 2.5 $m^2/g$, 2.6 $m^2/g$, 2.7 $m^2/g$, 2.8 $m^2/g$, 2.9 $m^2/g$, 3.0 $m^2/g$, 3.2 $m^2/g$, 3.4 $m^2/g$, 3.6 $m^2/g$, 3.8 $m^2/g$, 4.0 $m^2/g$, 4.2 $m^2/g$, 4.4 $m^2/g$, 4.6 $m^2/g$, 4.8 $m^2/g$, 5.0 $m^2/g$, 5.2 $m^2/g$, 5.4 $m^2/g$, 5.6 $m^2/g$, 5.8 $m^2/g$, 6.0 $m^2/g$, 6.2 $m^2/g$, 6.4 $m^2/g$, 6.6 $m^2/g$, 6.8 $m^2/g$, 7.0 $m^2/g$, 7.2 $m^2/g$, 7.4 $m^2/g$, 7.6 $m^2/g$, 7.8 $m^2/g$, 8.0 $m^2/g$, 8.2 $m^2/g$, 8.4 $m^2/g$, 8.6 $m^2/g$, 8.8 $m^2/g$, 9.0 $m^2/g$, 9.2 $m^2/g$, 9.4 $m^2/g$, 9.6 $m^2/g$, 9.8 $m^2/g$, 10.0 $m^2/g$, 11.0 $m^2/g$, 11.5 $m^2/g$, 12.0 $m^2/g$, 12.5 $m^2/g$, 13.0 $m^2/g$, 13.5 $m^2/g$, 14.0 $m^2/g$, 14.5 $m^2/g$, 15.0 $m^2/g$, 15.5 $m^2/g$, 16.0 $m^2/g$, 16.5 $m^2/g$, 17.0 $m^2/g$, 17.5 $m^2/g$, 18.0 $m^2/g$, 18.5 $m^2/g$, 19.0 $m^2/g$, 19.5 $m^2/g$, or 20.0 $m^2/g$. The specific surface area of the carrier can be, for example, more than about 1.3 $m^2/g$, 1.2 $m^2/g$, 1.4 $m^2/g$, 1.6 $m^2/g$, 1.8 $m^2/g$, 2 $m^2/g$, or 10 $m^2/g$; or about 1.3 $m^2/g$ to about 2 m²/g. In some embodiments, the specific surface area is measured by a gas adsorption method on the BET theory.

In some embodiments, a carrier can be added by blending, e.g., by container mixing such as v-blender, or vortex mixing. The duration of the blending can be, for example, about 1 min to 300 min, about 1 min to 240 min, about 1 min to 180 min, or about 5 min to 180 min. The duration of the blending can be, for example, more than about 1 min, 2 min, 5 min, 10 min, 15 min, 30 min, 45 min, 60 min, 90 min, 120 min, 180 min, 240 min or 300 min. The duration of the blending can be, for example, about 1 min, 5 min, 10 min, 15 min, 30 min, 45 min, 60 min, 75 min, 90 min, 120 min, 180 min, 240 min or 300 min.

V. Vaccine Compositions

In some aspects, a vaccine composition (e.g., in dry powder) is prepared by blending the freeze-dried antigen with the carrier excipient.

In some embodiments, an average particle size of the dry powder vaccine formulations can be measured by for example, sifting, sieving or laser diffraction. The average particle size of the dry powder vaccine formulations can be, e.g., between about 18 microns-500 microns, about 18 microns-300 microns, about 18 microns-200 microns, or about 18 microns-150 microns. In some embodiments, the vaccine compositions (e.g., in dry powder) described herein can have an average particle size of 20 microns, 50 microns, 75 microns, 100 microns or 150 microns, measured by, for example, laser diffraction, sieving or sifting.

In some embodiments, a vaccine composition (e.g., in dry powder) packaged in an airtight container can be stored (preserved) at a temperature of about 4 to 25 degrees C. The relative humidity of the preservation condition can be about 0% to 70%, about 0% to 60%, about 0% to 50%, about 0% to 40%, about 0% to 30%, about 0% to 20%, about 0% to 10%, or about 0% to 5%. The relative humidity of the preservation can be less than about 80%, 75%, 70%, 65%, 60%, 55%, 50%, 45%, 40%, 35%, 30%, 25%, 24%, 23%, 22%, 21%, 60%, 19%, 18%, 17%, 16%, 15%, 14%, 13%, 12%, 11%, 10%, 9%, 8%, 7%, 6%, 5%, 4%, 3%, 2%, or 1%.

In some embodiments, a water content of a vaccine composition can be about 10%, 9%, 8%, 7%, 6%, 5%, 4%, 3%, 2%, 1%, 0.5%, or 0.1%.

In some embodiments, a delivered weight of a vaccine composition from a mucosal delivery device can be more than 60%, 70%, 80% or 90%.

VI. Stability

In some aspects, a freeze-dried antigen as described herein in an air-tight container and a vaccine composition (e.g., in dry powder) prepared as described herein in an air-tight container can be stable at room temperature (25 degrees C. and 60% relative humidity) for at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36 months. The stability of the freeze-dried antigen as described herein in an air-tight container and the vaccine composition (e.g., in dry powder) in an air-tight container can also be stable under accelerated conditions (45 degrees C. and 75% relative humidity) for extended time periods. Under accelerated conditions, a freeze-dried antigen as described herein in an air-tight container and a vaccine composition (e.g., in dry powder) can be stable for at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36 months. A freeze-dried antigen as described herein in an air-tight container and a vaccine composition (e.g., in dry powder) prepared as described herein in the air-tight container can be stable at other temperatures (e.g., −20 degrees C. to 55 degrees C.) and relative humidity (0% to 100%). In some embodiments, about 80%-100% (e.g., about: 90%-100% or 95-100%) such as about: 80%, 90%, 95%, or 100% of an antigen in the composition remains intact, e.g., as measured by High Performance Liquid Chromatography (HPLC), for a period of time, e.g., at least about: 30 days, 60 days, 90 days, 6 months, 1 year, 18 months, 2 years, 3 years, 4 years, or 5 years. In some embodiments, a water content remains unchanged or does not acquire higher than 10% in the composition for a period of time, at least about: 30 days, 60 days, 90 days, 6 months, 1 year, 18 months, 2 years, 3 years, 4 years, or 5 years.

Stability, as used herein, can refer to several aspects of the freeze-dried antigen and the dry vaccine powder under storage conditions. One such aspect is antigenic potency, e.g., retention of antigenicity of the antigenic component of the vaccine. This aspect of stability, for example, of a freeze-dried antigen and a dry powder influenza vaccine composition comprising HA, can be determined by measuring hemagglutination (HA) reactivity by the HA assay, HA content by the single-radial immuno-diffusion (SRD) assay, or the hemagglutination inhibition assay or the neutralization assay with blood samples from an immunogenicity study in animals. A vaccine composition (e.g., in dry powder) is considered stable if it retains at least 50% antigenicity (compared to initial potency) after a particular time under particular conditions (e.g., 18 months under accelerated conditions).

VII. Routes and Means of Administration

In some embodiments, a device can be configured to deliver a substantial fraction of a single dose of a vaccine composition (e.g., in dry powder) on mucosa (e.g., nasal mucosa) of a subject. In some cases, a device may be configured to deliver a substantial fraction of an amount of a vaccine composition (e.g., in dry powder) residing within the device on the mucosa of a subject. In some cases, a vaccine composition (e.g., in dry powder) or a substantial fraction thereof may be delivered after a single engagement of the device. In some cases, a vaccine composition (e.g., in dry powder) or a substantial fraction thereof can be delivered after multiple engagements of the device, such as for example 1, 2, 3, 4, 5, 6, 7, 8, 9, or 10 engagements. In some cases, multiple engagements of a device may constitute a single use of a device. According to the methods, devices, and compositions described herein a substantial fraction of the vaccine composition (e.g., in dry powder) delivered by the device encompasses at least 50%, 55%, 60%, 65%, 70%, 75%, 80%, 85%, 90%, 91%, 92%, 93%, 94%, 95%, 96%, 97%, 97.5%, 98%, 98.5%, 99%, 99.5%, 99.9%, 99.95%, or 100% of the amount of vaccine composition (e.g., in dry powder) such as the amount in a single dose or the amount residing in the device.

In some embodiments, a composition herein is for intranasal, buccal, or oral administration. In some embodiments, a composition herein is dissolved or suspended in a liquid. In some embodiments, a composition herein can be formulated to be swallowed whole. In some embodiments, a composition herein is formulated as a dosage form (e.g., tablet, capsule, gel, lollipop), parenteral, intraspinal infusion, inhalation, nasal spray, transdermal patch, iontophoresis transport, absorbing gel, liquid, liquid tannate, suppository, injection (e.g., intravenous, intramuscular), I.V. drip, other formulation, or a combination thereof to treat subjects. In some embodiments, a composition herein is formulated as single oral dosage form such as a tablet, capsule, cachet, soft gelatin capsule, hard gelatin capsule, extended release capsule, tannate tablet, oral disintegrating tablet, multi-layer tablet, effervescent tablet, bead, liquid, oral suspension, chewable lozenge, oral solution, lozenge, lollipop, oral syrup, sterile packaged powder including pharmaceutically-acceptable excipients, other oral dosage forms, or a combination thereof. In some embodiments, a composition or an active agent herein is formulated for immediate-release, quick release, controlled-release, extended release, or a combination thereof.

VIII. Effects of Dry Powder Formulation on Immunity

In some aspects, a method or composition disclosed herein can be used to stimulate a local immune response. A local immune response can be in peripheral lymphoid tissue. For example, a vaccine composition (e.g., in dry powder) can be administered to the mucosal to stimulate mucosa-associated lymphoid tissue (MALT), which can play a role in mucosal immunity. Examples of mucosa include buccal mucosa, esophageal mucosa, gastric mucosa, intestinal mucosa, nasal mucosa, olfactory mucosa, oral mucosa, bronchial mucosa, uterine mucosa, endometrium (mucosa of the uterus), vaginal mucosa and penile mucosa. In particular, nasopharynx-associated lymphoid tissue (NALT) can be targeted. NALT can play a role in the generation of T helper 1 and T helper 2 cells, and IgA-committed B cells. Intranasal immunization can lead to the induction of antigen-specific protective immunity in both the mucosal and systemic immune compartments.

In some aspects, a method or composition disclosed herein can be used to stimulate production of the principal antibody of the mucosal immune system, secretory IgA (sIgA). sIgA is a dimer or tetramer composed of two or four monomers, a J-chain polypeptide, and a polypeptide chain called secretory component. The J-chain polypeptide can facilitate the polymerization of both serum and secretory IgA. The secretory component is a 70 kDa polypeptide produced by epithelial cells of mucous membranes and can protect sIgA by making it less susceptible to proteolytic enzymes in mucous secretions. sIgA can be produced locally by mucosal plasma cells that are descended from precursors initially stimulated in organized, mucosal lymphoid organs designed for antigen sampling. After an initial trigger, the precursor cells can pass via regional lymph nodes, lymph, and blood to disseminate widely among mucosal sites, thus leading to protection at mucosal sites other than the site of administration (e.g., nasal administration). After secretion from a local plasma cell, sIgA can bind to an epithelial cell surface receptor, and the complex can pass through the epithelial cell into the secretions where it can serves as a nonphlogistic immunologic barrier to inhibit uptake of antigens.

In some aspects, a method or composition disclosed herein can also stimulate an IgG response. Such stimulation can lead to an additional layer of protection, for example by priming the humoral response to react to a pathogen which eludes or evades the protection provided by the sIgA induced by a vaccine disclosed herein. Thus, in some embodiments, vaccines disclosed herein can induce both mucosal and humoral antibody responses.

IX. Evaluation of Freeze-Dried Products

In some aspects, cakes of the freeze-dried antigens and powders are visually inspected. In some embodiments, desirable cake appearance does not have one or more of shrinkage, cracking, collapse, or melt-back.

In some aspects, HA assay is used to evaluate hemagglutinating property of HA antigen. Samples of freeze-dried antigen are diluted, e.g., 1.0, 1.2, 1.4 and 1.7 fold, and each diluted sample additionally diluted, e.g., 2.0 fold serially diluted, and then mixed with an equal volume of chicken eggs RBCs in microtiter plates and screened the agglutination reaction to chicken eggs RBCs. The HA reactivity of vaccine in a freeze-dried antigen is determined as a residual HA titer when compared with the vaccine in a liquid form without freeze-drying, using the HA assay method. Residual HA titers (%) for freeze-dried antigens are calculated as the percentage of HA titer of freeze-dried antigen/HA titer of liquid form antigens without freeze-drying.

In some aspects, cake friability is evaluated to vibrate the vials with the freeze-dried antigens and powders using the vortex mixer or agitate the cake in the vial using a spatula.

In some aspects, water contents of freeze-dried antigens and powders are determined by the Karl Fischer's method.

EXAMPLES

Example 1: Preparations and Testing of Freeze-Dried Antigens (Influenza Split Vaccine Antigen) and Powders with Different Ratios of Trehalose and Mannitol In this example, various freeze-dried influenza split vaccine antigens and powder with different ratios of trehalose and mannitol were prepared and tested to evaluate their cake appearances, friability to result in fine particles, water content and HA reactivity.

Example 1A: Preparations of Freeze-Dried Influenza Split Vaccine Antigens and Powders with Different Ratios of Trehalose and Mannitol In this experiment, various ratios of trehalose and mannitol were used in a desired freeze-drying method to generate freeze-dried antigens and powders, which were then examined for their cake appearances, friability to result in fine particles, water content and HA reactivity. In a glass vial for freeze-drying, an appropriate volume of pH7.4 phosphate buffer saline with 1% salt concentration (pH7.4 1% PBS) was added to prepare final volume of 1 mL and then 500 mg/mL of trehalose dihaydrate (Wako pure chemical industries, Ltd.) dissolved in pH7.4 1% PBS and 150 mg/mL of D(−)-mannitol (Wako pure chemical industries, Ltd.) dissolved in 1% PBS were added in the vial as provided below.

| | Total amount of saccharides added per 1 mL of the liquid mixture | Trehalose/ Mannitol Ratio | Trehalose (500 mg/mL) | Mannitol (150 mg/mL) |
|---|---|---|---|---|
| PA-1 | 100 mg | 1:0 | 200 μL | 0 μL |
| PA-2 | | 4:1 | 160 μL | 133 μL |
| PA-3 | | 3:1 | 150 μL | 167 μL |
| PA-4 | | 1:1 | 100 μL | 333 μL |
| PA-5 | | 1:3 | 50 μL | 500 μL |
| PA-6 | | 1:4 | 40 μL | 533 μL |
| PA-7 | | 0:1 | 0 μL | 667 μL |

Three hundred and fifty micro L of influenza split vaccine (Influenza HA Vaccine "SEIKEN", trivalent, A/California/7/2009(H1N1)pdm09, A/New York/39/2012(H3N2), B/Massachusetts/2/2012, >90 micro g HA/mL of hemagglutinin, Denka Seiken co, Ltd.) was added in each the vial and mixed it to obtain liquid antigen mixtures. Additionally, 350 micro L of pH7.4 1% PBS (instead of influenza split vaccine) was added in each the vial and mixed it to obtain a liquid non-antigen mixture. The liquid antigen mixtures and the liquid non-antigen mixtures were freeze-dried to prepare freeze-dried antigens and powders at conditions provided below (Labconco Corp.).

| Step | Pre-set Temp (° C.) | Duration (hour) | Vacuum (mTorr) |
|---|---|---|---|
| Pre-freeze: | −30 | — | — |
| Sample pre-freeze: | −30 | 1.5 | — |
| Annealing: | −23 | 3.0 | — |
| Freezing: | −45 | 1.0 | 105 |
| 1st Drying: | −35 | 54.0 | 105 |
| 2nd Drying: | 30 | 4.0 | 105 |

Example 1B: Examinations for Freeze-Dried Antigens and Powders Prepared in Example 1A The freeze-dried antigens and powders prepared in Example 1A were examined for their cake appearances, friability to result in fine particles, water content and HA reactivity. Cakes of the freeze-dried antigens and powders and their visual inspection results are shown in FIG. 2. As shown in FIG. 2, compositions at trehalose/mannitol ratios of 1:1, 1:3, 1:4 and 0:1 for freeze-dried powders, and 1:1, 1:3 and 1:4 for freeze-dried antigens result in the desirable cake appearance which is neither shrinkage, cracking, collapse nor melt-back. The results of cake appearance, cake friability, water content and hemagglutination (HA) assay are summarized in Table 1. HA assay is a diagnostic tool used to evaluate hemagglutinating property of HA antigen. Samples of freeze-dried antigen were diluted 1.0, 1.2, 1.4 and 1.7 fold, and each diluted sample additionally were 2.0 fold serially diluted, and then mixed with an equal volume of chicken eggs RBCs in microtiter plates and screened the agglutination reaction to chicken eggs RBCs. The cake friability was evaluated to vibrate the vials with the freeze-dried antigens and powders using the vortex mixer or agitate the cake in the vial using a spatula. The water contents of the freeze-dried antigens and powders were determined by the Karl Fischer's method. The HA reactivity of split influenza vaccine in the freeze-dried antigen was determined as a residual HA titer when compared with the split influenza vaccine (liquid form without freeze-drying) using the HA assay method. Residual HA titers (%) for freeze-dried antigens were calculated as the percentage of HA titer of freeze-dried antigen/HA titer of liquid form antigens without freeze-drying.

As shown in Table 1, the freeze-dried antigens and powders with friable cake correlates them with the desirable cake appearance and the water contents of these freeze-dried antigens and powders was less than 5.3%. Additionally, the residual HA titers in freeze-dried antigens with trehalose as well as mannitol were more than 50%. These results indicate that the compositions prepared at trehalose/mannitol ratios of 1:1 to 1:4 with 100 mg of total saccharide amount are useful to obtain the desirable freeze-dried antigen and powder for mucosal delivery.

Example 2: Preparations and Testing of Freeze-Dried Powders with and without an Annealing Step In this example, various freeze-dried powder with different ratios of trehalose and mannitol were prepared using freeze-dry methods with and without an annealing step and tested to evaluate their cake appearances, friability to result in fine particles, water content and X-ray powder diffraction.

Example 2A: Preparations of Freeze-Dried Powders with and without an Annealing Step In this experiment, various ratios of trehalose and mannitol were used in the freeze-drying methods with and without an annealing step to generate freeze-dried powders, which were then examined for their cake appearances, friability to result in fine particles and water content. In a glass vial for freeze-drying, an appropriate volume of pH7.4 phosphate buffer saline with 1% salt concentration (pH7.4 1% PBS) was added to prepare final volume of 1 mL and then 500 mg/mL of trehalose dihaydrate (Wako pure chemical industries, Ltd.) dissolved in pH7.4 1% PBS and 150 mg/mL of D(−)-mannitol (Wako pure chemical industries, Ltd.) dissolved in 1% PBS were added in the vial as provided below.

| | Total amount of saccharides added per 1 mL of the liquid mixture | Trehalose/Mannitol Ratio | Trehalose (500 mg/mL) | Mannitol (150 mg/mL) |
|---|---|---|---|---|
| PA-8 | 100 mg | 1:0 | 200 μL | 0 μL |
| PA-9 | | 4:1 | 160 μL | 133 μL |
| PA-10 | | 3:1 | 150 μL | 167 μL |
| PA-11 | | 1:1 | 100 μL | 333 μL |
| PA-12 | | 1:3 | 50 μL | 500 μL |
| PA-13 | | 1:4 | 40 μL | 533 μL |
| PA-14 | | 0:1 | 0 μL | 667 μL |

TABLE 1

Effects of Trehalose/Mannitol Ratio on Freeze-Dried Antigen and Powder

| | | Total amount of saccharides added per 1 mL of the liquid mixture Trehalose/Mannitol Ratio | | | | | | |
|---|---|---|---|---|---|---|---|---|
| | | 100 mg 1:0 | 100 mg 4:1 | 100 mg 3:1 | 100 mg 1:1 | 100 mg 1:3 | 100 mg 1:4 | 100 mg 0:1 |
| w/o Antigen | Cake Appearance | Undesirable | Undesirable | Undesirable | Desirable | Desirable | Desirable | Desirable |
| | Easily Friable Cake | No | No | No | Yes | Yes | Yes | Yes |
| | Water Content (%) | 3.2 | 4.2 | 3.9 | 4.3 | 5.3 | 5.0 | 0.6 |
| w/ Antigen | Cake Appearance | Undesirable | Undesirable | Undesirable | Desirable | Desirable | Desirable | Undesirable |
| | Easily Friable Cake | No | No | No | Yes | Yes | Yes | No |
| | Water Content (%) | 6.5 | 7.2 | 7.4 | 3.9 | 4.9 | 4.8 | 5 |
| | HA Assay (residual HA titer, %) | 100 | 83 | 100 | 100 | 100 | 71 | 18 |

These vials were mixed to obtain a liquid non-antigen mixture. The liquid non-antigen mixtures were freeze-dried to prepare freeze-dried powders at conditions provided below (Labconco Corp.).

| Step | Pre-set Temp (° C.) | Duration (hour) | Vacuum (mTorr) |
|---|---|---|---|
| Pre-freeze: | −30 | — | — |
| Sample pre-freeze: | −30 | 1.5 | — |
| Annealing: | −23 or −30* | 3.0 | — |
| Freezing: | −45 | 1.0 | 105 |
| $1^{st}$ Drying: | −35 | 54.0 | 105 |
| $2^{nd}$ Drying: | 30 | 4.0 | 105 |

*Annealing at −30 C. corresponds to the freeze-dry method without an annealing step due to the same temperature as that for sample pre-freeze.

Example 2B: Examinations for Freeze-Dried Powder Prepared in Example 2A

The freeze-dried powders prepared in Example 2A were examined for their cake appearances, friability to result in fine particles and water content. Cakes of the freeze-dried powders and their visual inspection results are shown in FIG. 3. As shown in FIG. 3, compositions at trehalose/mannitol ratios of 1:1, 1:3, 1:4 and 0:1 for freeze-dried powder with 100 mg of total saccharide amount which were freeze-dried with the annealing step, and 1:3 and 1:4 for freeze-dried powders with 100 mg of total saccharide amount which were freeze-dried without the annealing step result in the desirable cake appearance which is neither shrinkage, cracking, collapse nor melt-back. The results of cake appearance, cake friability and water content are summarized in Table 2. The cake friability was evaluated to vibrate the vials with the freeze-dried antigens and powders using the vortex mixer or agitate the cake in the vial using a spatula. The water contents of the freeze-dried antigens and powders were determined by the Karl Fischer's method.

mulated in amorphous form since no specific peaks to identify crystal form of trehalose was observed. On the other hand, specific peaks to identify crystal form of mannitol were observed for the freeze-dried powder with and without annealing. As is obvious from FIG. 4, the heights of specific peaks for mannitol in the freeze-dried powders with annealing are greater than those without annealing. This indicates that the annealing in the freeze-dry method is useful to increase crystal form of mannitol. The relationship between ratios of mannitol to trehalose in the freeze-dried powders and the sums of heights for mannitol crystal is represented in FIG. 5. The crystallinity of mannitol was decreased with a decrease of mannitol ratio to trehalose. The crystallinity of mannitol at appropriate trehalose/mannitol ratios to obtain the desirable freeze-dried powder is approximately 40% for 1:1 ratio (50% mannitol content) and 80% for 1:4 ratio (80% mannitol content), respectively, when the sum of peak heights for mannitol crystal in the freeze-dried powder with 100% mannitol which was freeze-dried with annealing is represented as 100%.

Example 3: Preparations and Testing of Freeze-Dried Antigens (Influenza Split Vaccine Antigen) with Different Ratios and Amounts of Trehalose and Mannitol In this example, various freeze-dried influenza split vaccine antigens with different ratios and amounts of trehalose and mannitol were prepared and tested to evaluate their cake appearances, friability to result in fine particles and HA reactivity.

TABLE 2

Effects of Annealing on Freeze-Dried Powder

| | | Total amount of saccharides added per 1 mL of the liquid mixture Trehalose/Mannitol Ratio | | | | | | |
|---|---|---|---|---|---|---|---|---|
| | | 100 mg 1:0 | 100 mg 4:1 | 100 mg 3:1 | 100 mg 1:1 | 100 mg 1:3 | 100 mg 1:4 | 100 mg 0:1 |
| With Annealing | Cake Appearance | Undesirable | Undesirable | Undesirable | Desirable | Desirable | Desirable | Desirable |
| | Easily Friable Cake | No | No | No | Yes | Yes | Yes | Yes |
| | Water Content (%) | 3.2 | 4.2 | 3.9 | 4.3 | 5.3 | 5.0 | 0.6 |
| Without Annealing | Cake Appearance | Undesirable | Undesirable | Undesirable | Undesirable | Desirable | Desirable | Undesirable |
| | Easily Friable Cake | No | No | No | No | Yes | Yes | No |
| | Water Content (%) | 3.5 | 5.2 | 5.5 | 4.1 | 4.9 | 4.8 | 5.4 |

As shown in Table 2, the freeze-dried powders with friable cake correlates them with the desirable cake appearance and the water contents of these freeze-dried powders was equal to or less than 5.3%. These results indicate that the annealing step expanded a range of the effective trehalose/mannitol ratio to obtain the desirable freeze-dried powder for mucosal delivery.

Furthermore, X-ray powder diffraction (XRPD) analysis of the freeze-dried powders was conducted to evaluate formation states of amorphous and crystal for trehalose and mannitol in the freeze-dried powders. The XRPD patterns are shown in FIG. 4. It was found that trehalose in the freeze-dried powders with and without annealing was for- Example 3A: Preparations of Freeze-Dried Influenza Split Vaccine Antigens with Different Ratios and Amounts of Trehalose and Mannitol In this experiment, various ratios and amounts of trehalose and mannitol were used in a desired freeze-drying method to generate freeze-dried antigens, which were then examined for their cake appearances, friability to result in fine particles and HA reactivity. In a glass vial for freeze-drying, 500 mg/mL of trehalose dihaydrate (Wako pure chemical industries, Ltd.) dissolved in pH7.4 1% PBS and 150 mg/mL of D(−)-mannitol (Wako pure chemical industries, Ltd.) dissolved in 1% PBS were added in the vial as provided below.

|  | Total amount of saccharides added per 1 mL of the liquid mixture | Trehalose/ Mannitol Ratio | Trehalose (500 mg/mL) | Mannitol (150 mg/mL) |
|---|---|---|---|---|
| PA-15 | 100 mg | 1:0 | 200 µL | 0 µL |
| PA-16 | 100 mg | 7:1 | 175 µL | 83 µL |
| PA-17 | 100 mg | 3:1 | 150 µL | 167 µL |
| PA-18 | 100 mg | 2:1 | 133 µL | 222 µL |
| PA-19 | 100 mg | 1:1 | 100 µL | 333 µL |
| PA-20 | 100 mg | 1:2 | 67 µL | 444 µL |
| PA-21 | 100 mg | 1:3 | 50 µL | 500 µL |
| PA-22 | 100 mg | 1:7 | 25 µL | 583 µL |
| PA-23 | 75 mg | 1:0 | 131 µL | 63 µL |
| PA-24 | 75 mg | 7:1 | 113 µL | 125 µL |
| PA-25 | 75 mg | 3:1 | 100 µL | 167 µL |
| PA-26 | 75 mg | 2:1 | 75 µL | 250 µL |
| PA-27 | 75 mg | 1:1 | 50 µL | 333 µL |
| PA-28 | 75 mg | 1:2 | 38 µL | 375 µL |
| PA-29 | 75 mg | 1:3 | 19 µL | 438 µL |
| PA-30 | 50 mg | 1:0 | 100 µL | 0 µL |
| PA-31 | 50 mg | 7:1 | 88 µL | 42 µL |
| PA-32 | 50 mg | 3:1 | 75 µL | 83 µL |
| PA-33 | 50 mg | 2:1 | 67 µL | 111 µL |
| PA-34 | 50 mg | 1:1 | 50 µL | 167 µL |
| PA-35 | 50 mg | 1:2 | 33 µL | 222 µL |
| PA-36 | 50 mg | 1:3 | 25 µL | 250 µL |
| PA-37 | 50 mg | 1:7 | 13 µL | 292 µL |
| PA-38 | 50 mg | 0:1 | 0 µL | 333 µL |
| PA-39 | 30 mg | 1:0 | 60 µL | 0 µL |
| PA-40 | 30 mg | 1:1 | 30 µL | 100 µL |
| PA-41 | 30 mg | 1:2 | 20 µL | 133 µL |
| PA-42 | 30 mg | 1:3 | 15 µL | 150 µL |
| PA-43 | 30 mg | 1:7 | 8 µL | 175 µL |
| PA-44 | 20 mg | 1:0 | 40 µL | 0 µL |
| PA-45 | 20 mg | 1:1 | 20 µL | 67 µL |
| PA-46 | 20 mg | 1:2 | 13 µL | 89 µL |
| PA-47 | 20 mg | 1:3 | 10 µL | 100 µL |
| PA-48 | 20 mg | 1:7 | 5 µL | 117 µL |
| PA-49 | 10 mg | 1:0 | 20 µL | 0 µL |
| PA-50 | 10 mg | 1:3 | 5 µL | 50 µL |
| PA-51 | 10 mg | 1:7 | 2.5 µL | 58 µL |

Three hundred and fifty micro L of influenza split vaccine (Influenza HA Vaccine "SEIKEN", trivalent, A/California/7/2009(H1N1)pdm09, A/Victoria/361/2011(H3N2), B/Wisconsin/1/2010, >90 micro g HA/mL of hemagglutinin, Denka Seiken co, Ltd.) was added in each the vial, pH7.4 phosphate buffer saline with 1% salt concentration (pH7.4 1% PBS) was added to adjust 1 mL of the final volume in the vial and then mixed it to obtain liquid antigen mixtures. The liquid antigen mixtures were freeze-dried to prepare freeze-dried antigens and powders at conditions provided below (Labconco Corp.).

| Step | Pre-set Temp (° C.) | Duration (hour) | Vacuum (mTorr) |
|---|---|---|---|
| Pre-freeze: | −30 | — | — |
| Sample pre-freeze: | −30 | 1.5 | — |
| Annealing: | −23 | 3.0 | — |
| Freezing: | −45 | 1.0 | 105 |
| 1$^{st}$ Drying: | −35 | 54.0 | 105 |
| 2$^{nd}$ Drying: | 30 | 4.0 | 105 |

Example 3B: Examinations for Freeze-Dried Antigens Prepared in Example 3A

The freeze-dried antigens prepared in Example 3A were examined for their cake appearances, friability to result in fine particles and HA reactivity. The results of cake appearance, cake friability and HA assay are summarized in Table 3. The cake friability was evaluated to vibrate the vials with the freeze-dried antigens and powders using the vortex mixer or agitate the cake in the vial using a spatula. The HA reactivity of split influenza vaccine in the freeze-dried antigen was determined as a residual HA titer when compared with the split influenza vaccine (liquid form without freeze-drying) using the HA assay method.

TABLE 3

Effects of Trehalose/Mannitol Ratio and Amount on Freeze-Dried Antigen (Influenza Split Vaccine Antigen)

| | | Total amount of saccharides added per 1 mL of the liquid mixture Trehalose/Mannitol Ratio | | | | | | | |
|---|---|---|---|---|---|---|---|---|---|
| Freeze-Dried Influenza Split Vaccine Antigen | | 100 mg 1:0 | 100 mg 7:1 | 100 mg 3:1 | 100 mg 2:1 | 100 mg 1:1 | 100 mg 1:2 | 100 mg 1:3 | 100 mg 1:7 |
| w/ Antigen | Cake Appearance | Undesirable | Undesirable | Undesirable | Undesirable | Desirable | Desirable | Desirable | Desirable |
| | Easily Friable Cake | No | No | No | No | Yes | Yes | Yes | Yes |
| | HA Assay (residual HA titer, %) | NA | NA | NA | NA | 100 | 100 | 50 | 15 |

| | | Total amount of saccharides added per 1 mL of the liquid mixture Trehalose/Mannitol Ratio | | | | | | | |
|---|---|---|---|---|---|---|---|---|---|
| Freeze-Dried Influenza Split Vaccine Antigen | | 75 mg 1:0 | 75 mg 7:1 | 75 mg 3:1 | 75 mg 2:1 | 75 mg 1:1 | 75 mg 1:2 | 75 mg 1:3 | — |
| w/ Antigen | Cake Appearance | Undesirable | Undesirable | Undesirable | Undesirable | Desirable | Desirable | Desirable | — |
| | Easily Friable Cake | No | No | No | No | Yes | Yes | Yes | — |
| | HA Assay (residual HA titer, %) | NA | NA | NA | NA | 100 | 100 | 59 | — |

TABLE 3-continued

Effects of Trehalose/Mannitol Ratio and Amount on Freeze-Dried Antigen (Influenza Split Vaccine Antigen)

| | | \multicolumn{8}{c}{Total amount of saccharides added per 1 mL of the liquid mixture Trehalose/Mannitol Ratio} |
|---|---|---|---|---|---|---|---|---|---|
| \multicolumn{2}{l}{Freeze-Dried Influenza Split Vaccine Antigen} | 50 mg 1:0 | 50 mg 7:1 | 50 mg 3:1 | 50 mg 2:1 | 50 mg 1:1 | 50 mg 1:2 | 50 mg 1:3 | 50 mg 1:7 |
| w/ Antigen | Cake Appearance | Undesirable | Undesirable | Undesirable | Undesirable | Undesirable | Desirable | Desirable | Desirable |
| | Easily Friable Cake | No | No | No | No | No | Yes | Yes | Yes |
| | HA Assay (residual HA titer, %) | NA | NA | NA | NA | NA | 100 | 85 | 13 |

| | | \multicolumn{8}{c}{Total amount of saccharides added per 1 mL of the liquid mixture Trehalose/Mannitol Ratio} |
|---|---|---|---|---|---|---|---|---|---|
| \multicolumn{2}{l}{Freeze-Dried Influenza Split Vaccine Antigen} | 30 mg 1:0 | 30 mg 1:1 | 30 mg 1:2 | 30 mg 1:3 | 30 mg 1:7 | — | — | — |
| w/ Antigen | Cake Appearance | Undesirable | Undesirable | Undesirable | Undesirable | Undesirable | — | — | — |
| | Easily Friable Cake | No | No | No | No | Yes | — | — | — |
| | HA Assay (residual HA titer, %) | NA | NA | NA | NA | 100 | — | — | — |

| | | \multicolumn{8}{c}{Total amount of saccharides added per 1 mL of the liquid mixture Trehalose/Mannitol Ratio} |
|---|---|---|---|---|---|---|---|---|---|
| \multicolumn{2}{l}{Freeze-Dried Influenza Split Vaccine Antigen} | 20 mg 1:0 | 20 mg 1:1 | 20 mg 1:2 | 20 mg 1:3 | 20 mg 1:7 | — | — | — |
| w/ Antigen | Cake Appearance | Undesirable | Undesirable | Undesirable | Undesirable | Undesirable | — | — | — |
| | Easily Friable Cake | No | No | No | No | No | — | — | — |
| | HA Assay (residual HA titer, %) | NA | NA | NA | NA | NA | — | — | — |

| | | \multicolumn{8}{c}{Total amount of saccharides added per 1 mL of the liquid mixture Trehalose/Mannitol Ratio} |
|---|---|---|---|---|---|---|---|---|---|
| \multicolumn{2}{l}{Freeze-Dried Influenza Split Vaccine Antigen} | 10 mg 1:0 | 10 mg 1:3 | 10 mg 1:7 | — | — | — | — | — |
| w/ Antigen | Cake Appearance | Undesirable | Undesirable | Undesirable | — | — | — | — | — |
| | Easily Friable Cake | No | No | No | — | — | — | — | — |
| | HA Assay (residual HA titer, %) | NA | NA | NA | — | — | — | — | — |

As shown in Table 3, the freeze-dried antigens with friable cake correlate them with the desirable cake appearance. Additionally, the residual HA titers in freeze-dried antigens prepared at trehalose/mannitol ratios of 1:2 and 1:3 with more than 50 mg of total saccharide amount were more than 50%. These results indicate that the compositions prepared at trehalose/mannitol ratios of approximately 1:1 to 1:3 with more than 50 mg of total saccharide amount are useful to obtain the desirable freeze-dried antigen for mucosal delivery.

Example 4: Preparations and Testing of Freeze-Dried Antigens (Influenza Virosome Vaccine Antigen) with Different Ratios and Amounts of Trehalose and Mannitol In this example, various freeze-dried influenza virosome vaccine antigens with different ratios and amounts of trehalose and mannitol were prepared and tested to evaluate their cake appearances, friability to result in fine particles and HA reactivity.

Example 4A: Preparations of Freeze-Dried Influenza Virosome Vaccine Antigens with Different Ratios and Amounts of Trehalose and Mannitol In this experiment, various ratios and amounts of trehalose and mannitol were used in a desired freeze-drying method to generate freeze-dried antigens, which were then examined for their cake appearances, friability to result in fine particles and HA reactivity. In a glass vial for freeze-drying, 500 mg/mL of trehalose dihaydrate (Wako pure chemical industries, Ltd.) dissolved in pH7.4 1% PBS and 150 mg/mL of D(−)-mannitol (Wako pure chemical industries, Ltd.) dissolved in 1% PBS were added in the vial as provided below.

| | Total amount of saccharides added per 1 mL of the liquid mixture | Trehalose/ Mannitol Ratio | Trehalose (500 mg/mL) | Mannitol (150 mg/mL) |
|---|---|---|---|---|
| PA-52 | 100 mg | 1:1 | 100 μL | 333 μL |
| PA-53 | 75 mg | 1:1 | 75 μL | 250 μL |
| PA-54 | 75 mg | 1:2 | 50 μL | 333 μL |
| PA-55 | 50 mg | 1:2 | 33 μL | 222 μL |
| PA-56 | 50 mg | 1:1 | 50 μL | 167 μL |
| PA-57 | 30 mg | 1:1 | 30 μL | 100 μL |
| PA-58 | 30 mg | 1:2 | 20 μL | 133 μL |
| PA-59 | 0 mg | — | 0 μL | 0 μL |

Three hundred and fifty micro L of influenza virosome vaccine (Inflexal V, trivalent, A/California/7/2009(H1N1)-like, A/Victoria/361/2011(H3N2)-like, B/Massachusetts/2/2012-like, 90 micro g HA/mL, Crucell N.V.) was added in each the vial, pH7.4 phosphate buffer saline with 1% salt concentration (pH7.4 1% PBS) was added to adjust 1 mL of the final volume in the vial and then mixed it to obtain liquid antigen mixtures. The liquid antigen mixtures were freeze-dried to prepare freeze-dried antigens and powders at conditions provided below (Labconco Corp.).

| Step | Pre-set Temp (° C.) | Duration (hour) | Vacuum (mTorr) |
|---|---|---|---|
| Pre-freeze: | −30 | — | — |
| Sample pre-freeze: | −30 | 1.5 | — |
| Annealing: | −23 | 3.0 | — |
| Freezing: | −45 | 1.0 | 105 |
| 1$^{st}$ Drying: | −35 | 54.0 | 105 |
| 2$^{nd}$ Drying: | 30 | 4.0 | 105 |

Example 4B: Examinations for Freeze-Dried Antigens Prepared in Example 4A

The freeze-dried antigens prepared in Example 4A were examined for their cake appearances, friability to result in fine particles and HA reactivity. The results of cake appearance, cake friability and HA assay are summarized in Table 4. The cake friability was evaluated to vibrate the vials with the freeze-dried antigens and powders using the vortex mixer or agitate the cake in the vial using a spatula. The HA reactivity of split influenza vaccine in the freeze-dried antigen was determined as a residual HA titer when compared with the split influenza vaccine (liquid form without freeze-drying) using the HA assay method.

Example 5A: Preparations of Freeze-Dried Influenza Whole Inactive Vaccine Antigens with Ratio of Trehalose and Mannitol In this experiment, various ratios of trehalose and mannitol were used in a desired freeze-drying method to generate freeze-dried antigens, which were then examined for their cake appearances, friability to result in fine particles and HA reactivity. In a glass vial for freeze-drying, 500 mg/mL of trehalose dihaydrate (Wako pure chemical industries, Ltd.) dissolved in pH7.4 1% PBS and 150 mg/mL of D(−)-mannitol (Wako pure chemical industries, Ltd.) dissolved in 1% PBS were added in the vial as provided below.

| | Total amount of saccharides added per 1 mL of the liquid mixture | Trehalose/Mannitol Ratio | Trehalose (500 mg/mL) | Mannitol (150 mg/mL) |
|---|---|---|---|---|
| PA-60 | 100 mg | 1:1 | 100 μL | 333 μL |
| PA-61 | 0 mg | — | 0 μL | 0 μL |

Three hundred and fifty micro L of influenza whole inactive vaccine (A/Brisbane/59/2007(H1N1), 144 micro g HA/mL, Sinovac Biotech, Ltd.) was added in each the vial, pH7.4 phosphate buffer saline with 1% salt concentration (pH7.4 1% PBS) was added to adjust 1 mL of the final volume in the vial and then mixed it to obtain liquid antigen

TABLE 4

Effects of Trehalose/Mannitol Ratio and Amount on Freeze-Dried Antigen (Influenza Virosome Vaccine Antigen)

| | Freeze-Dried Influenza Virosome Vaccine Antigen | Total amount of saccharides added per 1 mL of the liquid mixture Trehalose/Mannitol Ratio | | | | | | | |
|---|---|---|---|---|---|---|---|---|---|
| | | 100 mg 1:1 | 75 mg 1:1 | 75 mg 1:2 | 50 mg 1:2 | 50 mg 1:1 | 30 mg 1:1 | 30 mg 1:2 | 0 mg — |
| w/ Antigen | Cake Appearance | Desirable | Desirable | Desirable | Desirable | Undesirable | Undesirable | Undesirable | Undesirable |
| | Easily Friable Cake | Yes | Yes | Yes | Yes | No | No | No | No |
| | HA Assay (residual HA titer, %) | 85 | 85 | 70 | 70 | 85 | 85 | 85 | 3 |

As shown in Table 4, the freeze-dried antigens with friable cake correlate them with the desirable cake appearance. Additionally, the residual HA titers in freeze-dried antigens with trehalose and mannitol were more than 50% although the freeze-dried antigens prepared with 30 mg of total saccharide amount and a trehalose/mannitol ratio of 1:1 with 50 mg of total saccharide amount have undesired cakes. These results indicate that the compositions prepared at trehalose/mannitol ratios of 1:1 with 100 mg of total saccharide, at trehalose/mannitol ratios of 1:1 to 1:2 with 75 mg of total saccharide amount and at a trehalose/mannitol ratio of 1:2 with 50 mg of total saccharide amount are useful to obtain the desirable freeze-dried antigen for mucosal delivery.

Example 5: Preparations and Testing of Freeze-Dried Antigens (Influenza Whole Inactive Vaccine Antigen) with Ratio of Trehalose and Mannitol In this example, various freeze-dried influenza whole inactive vaccine antigens with ratio of trehalose and mannitol were prepared and tested to evaluate their cake appearances, friability to result in fine particles and HA reactivity.

mixtures. The liquid antigen mixtures were freeze-dried to prepare freeze-dried antigens and powders at conditions provided below (Labconco Corp.)

| Step | Pre-set Temp (° C.) | Duration (hour) | Vacuum (mTorr) |
|---|---|---|---|
| Pre-freeze: | −30 | — | — |
| Sample pre-freeze: | −30 | 1.5 | — |
| Annealing: | −23 | 3.0 | — |
| Freezing: | −45 | 1.0 | 105 |
| 1$^{st}$ Drying: | −35 | 54.0 | 105 |
| 2$^{nd}$ Drying: | 30 | 4.0 | 105 |

Example 5B: Examinations for Freeze-Dried Antigens Prepared in Example 5A

The freeze-dried antigens prepared in Example 5A were examined for their cake appearances, friability to result in fine particles and HA reactivity. The results of cake appearance, cake friability and HA assay are summarized in Table 5. The cake friability was evaluated to vibrate the vials with the freeze-dried antigens and powders using the vortex mixer or agitate the cake in the vial using a spatula. The HA reactivity of influenza whole inactive vaccine in the freeze-dried antigen was determined as a residual HA titer when compared with the split influenza vaccine (liquid form without freeze-drying) using the HA assay method.

TABLE 5

Effects of Trehalose/Mannitol Ratio and Amount on Freeze-
Dried Antigen (Influenza Whole Inactive Vaccine Antigen)

| | | Total amount of saccharides added per 1 mL of the liquid mixture Trehalose/Mannitol Ratio | | | | | | | |
|---|---|---|---|---|---|---|---|---|---|
| Freeze-Dried Influenza Whole Inactive Vaccine Antigen | | 100 mg 1:1 | 0 mg — | — | — | — | — | — | — |
| w/ Antigen | Cake Appearance | Desirable | Undesirable | — | — | — | — | — | — |
| | Easily Friable Cake | Yes | No | — | — | — | — | — | — |
| | HA Assay (residual HA titer, %) | 100 | 0 | — | — | — | — | — | — |

As shown in Table 5, the composition prepared at a trehalose/mannitol ratio of 1:1 with 100 mg of total saccharide amount is useful to obtain the desirable freeze-dried antigen for mucosal delivery.

Example 6: Preparations and Testing of Vaccine Compositions (e.g., in Dry Powder) (Influenza Virosome Vaccine Antigen)

In this example, dry powder influenza virosome vaccine compositions were prepared and tested to evaluate their powder appearances, water content, HA reactivity and delivered weight from a mucosal delivery device.

Example 6A: Preparations of Freeze-Dried Influenza Virosome Vaccine Antigens In this experiment, freeze-dried antigens were used in a desired freeze-drying method and then examined for their cake appearances, friability to result in fine particles and HA reactivity. In a glass vial for freeze-drying, 500 mg/mL of trehalose dihaydrate (Wako pure chemical industries, Ltd.) dissolved in pH7.4 1% PBS and 150 mg/mL of D(−)-mannitol (Wako pure chemical industries, Ltd.) dissolved in 1% PBS were added in the vial as provided below.

| | Total amount of saccharides added per 1 mL of the liquid mixture | Trehalose/ Mannitol Ratio | Trehalose (500 mg/mL) | Mannitol (150 mg/mL) |
|---|---|---|---|---|
| PA-62 | 100 mg | 1:1 | 100 μL | 333 μL |
| PA-63 | 0 mg | — | 0 μL | 0 μL |

Three hundred and fifty micro L of influenza virosome vaccine (Inflexal V, trivalent, A/California/7/2009(H1N1)-like, A/Victoria/361/2011(H3N2)-like, B/Massachusetts/2/2012-like, 90 micro g HA/mL, Crucell N.V.) was added in each the vial, pH7.4 phosphate buffer saline with 1% salt concentration (pH7.4 1% PBS) was added to adjust 1 mL of the final volume in the vial and then mixed it to obtain liquid antigen mixtures. The liquid antigen mixtures were freeze-dried to prepare freeze-dried antigens and powders at conditions provided below (Labconco Corp.)

| Step | Pre-set Temp (° C.) | Duration (hour) | Vacuum (mTorr) |
|---|---|---|---|
| Pre-freeze: | −30 | — | — |
| Sample pre-freeze: | −30 | 1.5 | — |
| Annealing: | −23 | 3.0 | — |
| Freezing: | −45 | 1.0 | 105 |
| $1^{st}$ Drying: | −35 | 54.0 | 105 |
| $2^{nd}$ Drying: | 30 | 4.0 | 105 |

Example 6B: Examinations for Freeze-Dried Antigens Prepared in Example 6A

The freeze-dried antigens prepared in Example 6A were examined for their cake appearances, friability to result in fine particles and HA reactivity. The results of cake appearance, cake friability, water content and HA assay are summarized in Table 6. The cake friability was evaluated to vibrate the vials with the freeze-dried antigens and powders using the vortex mixer or agitate the cake in the vial using a spatula. The water contents of the freeze-dried antigens and powders were determined by the Karl Fischer's method. The HA reactivity of influenza virosome vaccine in the freeze-dried antigen was determined as a residual HA titer when compared with the split influenza vaccine (liquid form without freeze-drying) using the HA assay method.

TABLE 6

| Test Results of Freeze-Dried Antigen (Influenza Virosome Vaccine Antigen) | | | | | | | | | |
|---|---|---|---|---|---|---|---|---|---|
| | | Total amount of saccharides added per 1 mL of the liquid mixture Trehalose/Mannitol Ratio | | | | | | | |
| Freeze-Dried Influenza Virosome Vaccine Antigen | | 100 mg 1:1 | 0 mg — | — | — | — | — | — | — |
| w/ Antigen | Cake Appearance | Desirable | Undesirable | — | — | — | — | — | — |
| | Easily Friable Cake | Yes | No | — | — | — | — | — | — |
| | Water Content (%) | 5.3 | — | — | — | — | — | — | — |
| | HA Assay (residual HA titer, %) | 83 | 0 | — | — | — | — | — | — |

As shown in Table 6, the desirable freeze-dried antigen used for vaccine compositions (e.g., in dry powder) was obtained from the composition prepared at a trehalose/mannitol ratio of 1:1 with 100 mg of total saccharide amount.

Example 6C: Preparation of Vaccine Composition (e.g., in Dry Powder) Using Freeze-Dried Influenza Virosome Vaccine Antigens In this experiment, the vaccine composition (e.g., in dry powder) was prepared by blending the freeze-dried antigen prepared in Example 6A with two types of microcrystalline cellulose and tribasic calcium phosphate using vortex mixing as provided below.

| | Vaccine composition (e.g., in dry powder) | Freeze-Dried Antigen | | Microcrystalline Cellulose, Ceolus ® PH-F20JP | Microcrystalline Cellulose, Ceolus ® PH-301 | Tribasic Calcium Phosphate |
|---|---|---|---|---|---|---|
| VF-1 | Dry powder virosome vaccine composition (w/ trehalose/mannitol) | PA-62 | 315 mg | 1694 mg | 225 mg | 18.2 mg |
| VF-2 | Dry powder virosome vaccine composition (w/o trehalose/mannitol) | PA-63 | 18.65 mg | 1156 mg | 131 mg | 10.5 mg |

The vaccine composition (e.g., in dry powder) was packaged in the air-tight glass vials and stored at 4, 25 and 40 C. The vaccine composition (e.g., in dry powder) was examined for visual inspection for powder appearance, water content, HA assay, delivered weight from the nasal delivery device (Fit-lizer A delivery device, SNBL, Ltd.) or immunogenicity study in mice.

Example 6D: Initial Tests for Vaccine Compositions (e.g., in Dry Powder) Prepared in Example 6C The vaccine compositions (e.g., in dry powder) prepared in Example 6C were examined for visual inspection for powder appearance, water content, HA assay and delivered weight from the nasal delivery device (Fit-lizer A delivery device, SNBL, Ltd.). HA assay is a diagnostic tool used to evaluate hemagglutinaiting property of HA antigen. Samples of vaccine compositions (e.g., in dry powder) were diluted 1.0, 1.2, 1.4 and 1.7 fold, and each diluted sample additionally were 2.0 fold serially diluted, and then mixed with an equal volume of chicken eggs RBCs in microtiter plates and screened the agglutination reaction to chicken eggs RBCs. The test results are listed in Table 7. For both test samples, fine power appearance, water content of less than 6% and high delivered weight were observed. However, a residual HA titer of the VF-2 sample which were prepared without trehalose and mannitol is low due to the decreased antigenic potency (A residual HA titer for dry powder influenza virosome vaccine composition is detected as approximately 50% even if no antigenic potency is retained). Residual HA titers (%) for dry powder virosome vaccine composition were calculated as the percentage of HA titer of dry powder virosome vaccine composition/HA titer of liquid form virosome vaccine mixed with trehalose, mannitol and two types of microcrystalline cellulose, and tribasic calcium phosphate. The ratios and amounts of trehalose, mannitol and two types of microcrystalline cellulose, and tribasic calcium phosphate in sample of liquid form virosome vaccine is same as in sample of dry powder virosome vaccine composition.

TABLE 7

Initial Test Results of Vaccine composition (e.g., in dry powder) (Influenza Virosome Vaccine Antigen)

| | Test Item | | | |
|---|---|---|---|---|
| Test Sample | Visual Inspection | Water Content | HA Assay (Residual HA Titer) | Delivered Weight |
| VF-1: Dry Powder virosome vaccine composition (w/ trehalose/mannitol) | Fine Powder | 5.3% | 127% | 95% |
| VF-2: Dry Powder virosome vaccine composition (w/o trehalose/mannitol) | Fine Powder | 4.3% | 47% | 93% |

Example 6E: Stability Tests for Vaccine Compositions (e.g., in Dry Powder) Prepared in Example 6C The vaccine composition (e.g., in dry powder) prepared in Example 6C storage at 4, 25 and 40 degrees C. were examined for visual inspection for powder appearance and HA assay. The test results are listed in Table 8. The VF-1 samples stored at 4, 25 and 40 degrees C. were fine powder after approximately 30 days and their residual HA titers were more than 100% after approximately 30 or 60 days.

TABLE 8

Stability Test Results of Vaccine composition (e.g.,
in dry powder) (Influenza Virosome Vaccine Antigen)

| Test Sample | Storage Temp (° C.) | Visual Inspection @Test Day | Water Content @Test Day | HA Assay (Residual HA Titer) @Test Day | Delivered Weight @Test Day |
|---|---|---|---|---|---|
| VF-1: Dry powder Influenza virosome vaccine composition (w/ trehalose/ mannitol) | 4 | Fine Powder @Day 28 | — | 150% @Day 32 | — |
| | 25 | Fine Powder @Day 28 | — | 135% @Day 69 | — |
| | 40 | Fine Powder @Day 28 | — | 135% @Day 69 | — |

Example 6F: Mice Immunogenicity Study for Vaccine Compositions (e.g., in Dry Powder) Prepared in Example 6C Storage at 4, 25 and 40 Degrees C The immunogenicity of vaccine compositions (e.g., in dry powder) prepared in Example 6C were assessed in BALB/cCRSlc mice.

| | Vaccine Composition | Antigen | Trehalose | Mannitol | Microcrystalline Cellulose, Ceolus ® PH-F20JP | Microcrystalline Cellulose, Ceolus ® PH-301 | Tribasic Calcium Phosphate |
|---|---|---|---|---|---|---|---|
| VF-1 | Dry Powder Influenza Virosome Vaccine Composition (w/ trehalose/mannitol) | 2.5 mg | 3.97 mg | 3.97 mg | 46.93 mg | 6.25 mg | 0.5 mg |
| VF-2 | Dry Powder Influenza Virosome Vaccine Composition (w/o trehalose/mannitol) | 2.5 mg | — | — | 46.93 mg | 6.25 mg | 0.5 mg |
| Positive control | Liquid Form Influenza Virosome Vaccine Composition (w/ trehalose/mannitol) | 2.5 mg | 3.97 mg | 3.97 mg | 46.93 mg | 6.25 mg | 0.5 mg |

Mice were received one intraperitoneal dose of VF-1, VF-2, and positive control. Positive control as liquid form influenza virosome vaccine (intact Inflexal V) was mixed with trehalose, mannitol and two types of microcrystalline cellulose, and tribasic calcium phosphate. Bloods were collected and serums were prepared on days 28 after dosing. Immunogenicity of VF-1, VF-2 and positive control was determined using the hemagglutination inhibition (HI) assay. The HI assay results showed that GMT were 160.0 for VF-1 storage at 4 degrees C., 226.3 for VF-1 storage at 25 degrees C., 226.3 for VF-1 storage at 40 degrees C., and 139.3 for positive control storage at 4 degrees C., respectively.

TABLE 9

HI titers for VF1 storage at 4° C., 25° C. and 40° C. treated in mice

| | Storage (° C.) | Dose(μg HA/animal) | HI Titers Animal No. 1 | 2 | 3 | 4 | 5 | GMT | Geometric standard deviation | 95% confidence interval |
|---|---|---|---|---|---|---|---|---|---|---|
| VF-1 | 4 | 2.5 | 80 | 320 | 80 | 160 | 320 | 160.0 | 2.00 | 67.7-378.4 |
| | 25 | | 160 | 160 | 320 | 320 | — | 226.3 | 1.49 | 119.7-427.7 |
| | 40 | | 320 | 80 | 640 | 160 | — | 226.3 | 2.45 | 54.5-939.8 |

TABLE 9-continued

HI titers for VF1 storage at 4° C., 25° C. and 40° C. treated in mice

| Storage (° C.) | Dose(μg HA/animal) | HI Titers Animal No. | | | | | GMT | Geometric standard deviation | 95% confidence interval |
|---|---|---|---|---|---|---|---|---|---|
| | | 1 | 2 | 3 | 4 | 5 | | | |
| VF-2 | 4 | 2.5 | 40 | 80 | 20 | 40 | 80 | 45.9 | 1.79 | 22.4-94.4 |
| Positive Control | 4 | 2.5 | 160 | 80 | 160 | 160 | 160 | 139.3 | 1.36 | 94.8-204.7 |

As shown in Table 9, VF-1 storage at 4, 25 and 40 degrees C. on Days 28 were sufficient to elicit HI titers greater than or equal to 160, therefore VF1 have immunogenic in mice equal to positive control. The result suggests that VF-1, the dry powder composition with influenza virosome vaccine antigen in the present disclosure, retained its antigenic potency for at least 1 month at 4, 25 and 40 degrees C.

Example 7: Preparations of Freeze-Dried Compositions with Different Ratios of a First Saccharide and a Second Saccharide Various ratios of a first saccharide and a second saccharide are used to generate freeze-dried compositions, which are then examined for their cake appearances, friability to result in fine particles, water content and HA reactivity, using the same protocols as in the preceding examples. A first saccharide comprises 1, 2, 3, 4, 5, 6, 7, or 8 saccharides selected from the group consisting of trehalose, inulin, sucrose, maltose, isomaltose, maltotriose, pullulan, raffinose, or any combination thereof. A second saccharide comprises 1, 2, 3, or 4 saccharides selected from the group consisting of mannitol, sorbitol, glucose, galactose, or any combination thereof.

Example 8: Comparison of Immunogenicity of the Vaccine Compositions

A vaccine composition (e.g., nasal powder) disclosed herein is tested to elicit an immune response, in comparison to a liquid formulation. The vaccine is prepared using a freeze-dry method with annealing and blending with microcrystalline cellulose carriers, as explained supra. A same amount of antigen is administered to 2 groups of cynomolgus monkeys: Group 1—the present composition; Group 2—the liquid formulation.

Antibody levels in serum and nasal wash samples are determined by hemagglutination inhibition (HI) and enzyme-linked immunosorbent assay (ELISA). Samples are treated with Receptor Destroying Enzyme (RDE, Denka Seiken Co Ltd., Tokyo, Japan), e.g., for 15 to 18 hours at 37 degrees C. and then heat inactivated for 1 hour at 56 degrees C. Two-fold serial dilution series of the samples are prepared, mixed with HA antigen (Denka Seiken) at a concentration of e.g., 4 hemagglutination units per well, and incubated for e.g., 1 hour at room temperature. To each well, chicken red blood cells, e.g., 50 micro L of a 0.5% suspension, are added and hemagglutination is assessed an hour later. The highest dilution of sample that inhibits hemagglutination is the HI title of the sample.

Enzyme-linked immunosorbent assay (ELISA) antibody titers in serum and nasal wash samples are determined as follows. ELISA plates are coated with an antigen, e.g., for 17 hours at 4 degrees C., washed, and blocked, e.g., in 100 micro L of blocking solution (0.5% bovine serum albumin in phosphate buffer) for 1 hour at room temperature. After washing, 2-fold serial dilutions of the test samples are made in 0.5% BSA and PBS and the dilutions are added to the wells of the ELISA plate. After an incubation at 37 degrees C. for 1 hour, the plates are washed and incubated with a horseradish peroxidase (HRP)-conjugated goat anti-monkey IgG or HRP-conjugated sheep anti-monkey secretory component detection antiserum for 1 hour at 37 degrees C. The plates are then washed, incubated with o-Phenylenediamine (OPD) for 15 minutes at 37 degrees C., and the color reaction stopped by the addition of 100 micro L of 1M sulfuric acid ($H_2SO_4$). The samples are measured by OD492 on an ELISA reader.

While various embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A vaccine composition, wherein the vaccine composition is in a solid form and comprises:

an antigen;

a first saccharide, wherein the first saccharide is trehalose;

a second saccharide, wherein the second saccharide is mannitol; and a third saccharide that comprises microcrystalline cellulose, wherein: a weight ratio of the first saccharide to the second saccharide is from about 1:1 to about 1:5, or a molar ratio of the first saccharide to the second saccharide is from about 1:2 to about 1:10.

2. The vaccine composition of claim 1, which, when administered intranasally to a human, produces a serum immune response.

3. The vaccine composition of claim 1, which, when administered intranasally to a human, stimulates a production of a serum Immunoglobulin G (IgG) antibody.

4. The vaccine composition of claim 1, which, when administered intranasally to a human, produces a mucosal immune response.

5. The vaccine composition of claim 1, which, when administered intranasally to a human, stimulates a production of a mucosal secretory Immunoglobulin A (sIgA) antibody.

6. The vaccine composition of claim 1, which, when administered intranasally to a human, produces a cellular immune response.

7. The vaccine composition of claim 1, having the weight ratio of the first saccharide to the second saccharide that is about: 1:1, 1:2, 1:3, or 1:4.

8. The vaccine composition of claim 1, having the molar ratio of the first saccharide to the second saccharide which is about: 1:1, 2:3, 1:2, or 2:7.

9. The vaccine composition of claim 1, wherein at least 80% (w/w) of the first saccharide is in an amorphous form as measured by an X-ray powder diffraction analysis.

10. The vaccine composition of claim 1, wherein at least 20% (w/w) of the second saccharide is in a crystal form as measured by an X-ray powder diffraction analysis.

11. The vaccine composition of claim 1, wherein the microcrystalline cellulose has an average particle size from about 10 microns to about 100 microns as measured by sifting, sieving, or laser diffraction.

12. The vaccine composition of claim 1, wherein the antigen comprises a viral antigen, a bacterial antigen, or a combination thereof.

13. The vaccine composition of claim 1, wherein the antigen comprises live attenuated virus, whole inactivated virus, split virus, subunit antigen, virosome, antigenic protein, antigenic peptide, virus-like particle with antigenic protein, virus-like particle with antigenic peptide, cold-adapted live virus, killed whole bacteria, attenuated bacteria, bacterial toxoid, bacterial antigenic polysaccharide, nucleotide, phage, or any combination thereof.

14. The vaccine composition of claim 1, wherein the antigen comprises influenza virus, respiratory syncytial virus, Rhinovirus, Coronavirus, Adenovirus, metapneumovirus, bocavirus, parainfluenza virus, measles virus, rubella virus, varicella zoster virus, herpes simplex virus, human herpes virus, Parvovirus B19, Enterovirus, mumps virus, or any combination thereof.

15. The vaccine composition of claim 1, wherein the antigen comprises human papillomavirus, poliovirus, Rotavirus, Norwalk virus, sapovirus, Astrovirus, or any combination thereof.

16. The vaccine composition of claim 1, wherein the antigen comprises an influenza split virus.

17. The vaccine composition of claim 1, wherein the antigen comprises an influenza virosome.

18. The vaccine composition of claim 1, wherein the antigen comprises a whole inactivated influenza virus.

19. The vaccine composition of claim 1, wherein the vaccine composition further comprises an adjuvant.

20. A vaccine composition of claim 1, for intranasal administration.

21. A device that comprises a vaccine composition of claim 1.

22. The vaccine composition of claim 1, wherein a total amount of the first saccharide and the second saccharide is from about 45 mg to about 150 mg.

23. The vaccine composition of claim 1, wherein a total amount of the first saccharide and the second saccharide is about 50 mg, about 75 mg, or about 100 mg.

24. The vaccine composition of claim 1, having the weight ratio of the first saccharide to the second saccharide that is from about 1:1 to about 1:4.

25. The vaccine composition of claim 1, wherein: the antigen is a split virus antigen, the first saccharide and the second saccharide have a weight ratio of from about 1:1 to about 1:4, and a total amount of the first saccharide and the second saccharide is about 100 mg.

26. The vaccine composition of claim 1, wherein: the antigen is a virosome antigen, the first saccharide and the second saccharide have a weight ratio of about 1:1, and a total amount of the first saccharide and the second saccharide is about 100 mg.

27. The vaccine composition of claim 1, wherein: the antigen is a virosome antigen, the first saccharide and the second saccharide have a weight ratio of from about 1:1 to about 1:2, and a total amount of the first saccharide and the second saccharide is about 75 mg.

28. The vaccine composition of claim 1, wherein: the antigen is a virosome antigen, the first saccharide and the second saccharide have a weight ratio of about 1:2, and a total amount of the first saccharide and the second saccharide is about 50 mg.

29. The vaccine composition of claim 1, wherein: the antigen is a whole inactive virus antigen, the first saccharide and the second saccharide have a weight ratio of about 1:1, and a total amount of the first saccharide and the second saccharide is about 100 mg.

30. The vaccine composition of claim 1, wherein the vaccine composition is in a solid form of cake.

31. The vaccine composition of claim 1, wherein the vaccine composition is in a solid form of powder.

32. The vaccine composition of claim 1, having the weight ratio of the first saccharide to the second saccharide from about 1:1 to about 1:5.

33. The vaccine composition of claim 1, having the molar ratio of the first saccharide to the second saccharide from about 1:2 to about 1:10.

* * * * *